US011185600B2

(12) United States Patent
Figdor et al.

(10) Patent No.: US 11,185,600 B2
(45) Date of Patent: Nov. 30, 2021

(54) CONTRAST AGENT AND ITS USE FOR IMAGING

(71) Applicant: STICHTING RADBOUD UNIVERSITAIR MEDISCH CENTRUM, Nijmegen (NL)

(72) Inventors: Carl Gustav Figdor, 's-Hertogenbosch (NL); Ingrid Jolanda Monique De Vries, Nijmegen (NL); Mangala Srinivas, Utrecht (NL); Luis Javier Cruz Ricondo, Nijmegen (NL); Christoffel Leendert De Korte, Zeist (NL)

(73) Assignee: STICHTING RADBOUD UNIVERSITAIR MEDISCH CENTRUM, Nijmegen (NL)

( * ) Notice: Subject to any disclaimer, the term of this patent is extended or adjusted under 35 U.S.C. 154(b) by 134 days.

(21) Appl. No.: 14/428,350

(22) PCT Filed: Sep. 14, 2013

(86) PCT No.: PCT/EP2013/069079
§ 371 (c)(1),
(2) Date: Mar. 13, 2015

(87) PCT Pub. No.: WO2014/041150
PCT Pub. Date: Mar. 20, 2014

(65) Prior Publication Data
US 2015/0250905 A1 Sep. 10, 2015

(30) Foreign Application Priority Data
Sep. 14, 2012 (EP) .................................... 12184562

(51) Int. Cl.
*A61B 8/00* (2006.01)
*A61K 49/22* (2006.01)
*A61K 49/18* (2006.01)
*A61K 49/00* (2006.01)

(52) U.S. Cl.
CPC ........ *A61K 49/225* (2013.01); *A61K 49/0002* (2013.01); *A61K 49/0034* (2013.01); *A61K 49/0093* (2013.01); *A61K 49/1818* (2013.01); *A61K 49/221* (2013.01)

(58) Field of Classification Search
None
See application file for complete search history.

(56) References Cited

U.S. PATENT DOCUMENTS

| 2003/0004533 | A1* | 1/2003 | Dieck ............. A61B 17/12022 606/191 |
| 2005/0240098 | A1* | 10/2005 | Zhong ................. G01R 33/285 600/410 |
| 2010/0158815 | A1 | 6/2010 | Wang et al. |
| 2011/0020239 | A1 | 1/2011 | Bulte et al. |
| 2011/0177005 | A1* | 7/2011 | Rapoport ............. A61K 9/0009 424/9.37 |

FOREIGN PATENT DOCUMENTS

| CN | 101574530 A | 11/2009 | |
| JP | 2010022690 A | 2/2010 | |
| WO | 9921592 A1 | 5/1999 | |
| WO | 0071172 A1 | 11/2000 | |
| WO | 2005072780 A2 | 8/2005 | |
| WO | 2008144028 A1 | 11/2008 | |
| WO | 2012113733 A1 | 8/2012 | |
| WO | WO2012/113733 A1 * | 8/2012 | ............. A61K 47/48 |
| WO | 2014041150 A1 | 3/2014 | |

OTHER PUBLICATIONS

Acharya et al. (Adv. Drug Delivery Rev. 2011, 63, 170-183).*
Ao et al. (J. Biomed. Mater. Res. Part B: Appl. Biomater. 2010, 93B, 551-556).*
Qin, Ruogu Intraoperative Imaging Platform, Graduate Program in Biomedical Engineering, The Ohio State University, 2011.*
Morawski et al. (Mag. Reson. Med. 2004, 52, 1255-1262).*
Neubauer et al. (Mag. Reson. Med. 2008, 60, 1066-1072).*
Pisani et al. (Langmuir 2006, 22, 4397-4402).*
Miller et al. (J. Ultrasound Med. 2012, 623-634, provided as p. 1-16).*

(Continued)

*Primary Examiner* — Michael G. Hartley
*Assistant Examiner* — Melissa J Perreira
(74) *Attorney, Agent, or Firm* — Hudak, Shunk & Farine Co. LPA

(57) ABSTRACT

The present invention relates to contrast agent enhanced medical ultrasound imaging. In particular, the contrast agents provided are useful for cell imaging and cell therapy, as well as in vivo targeting, drug delivery and perfusion or vascular imaging applications. More specifically, it provides a particle comprising a fluorinated organic compound and a metal. Such particles may be advantageously employed in qualitative or quantitative imaging such as acoustic imaging including photoacoustic and ultrasound imaging, MRI imaging, such as 19F imaging, 1H imaging including T1 and T2 weighted imaging, SPECT, PET, scintigraphy, fluorescence imaging and optical coherence imaging and tomographic applications. This may then be employed in cell labeling, microscopy, histology or for imaging vasculature or perfusion in vivo and in vitro.

13 Claims, 40 Drawing Sheets

(56) References Cited

OTHER PUBLICATIONS

Figure 1:
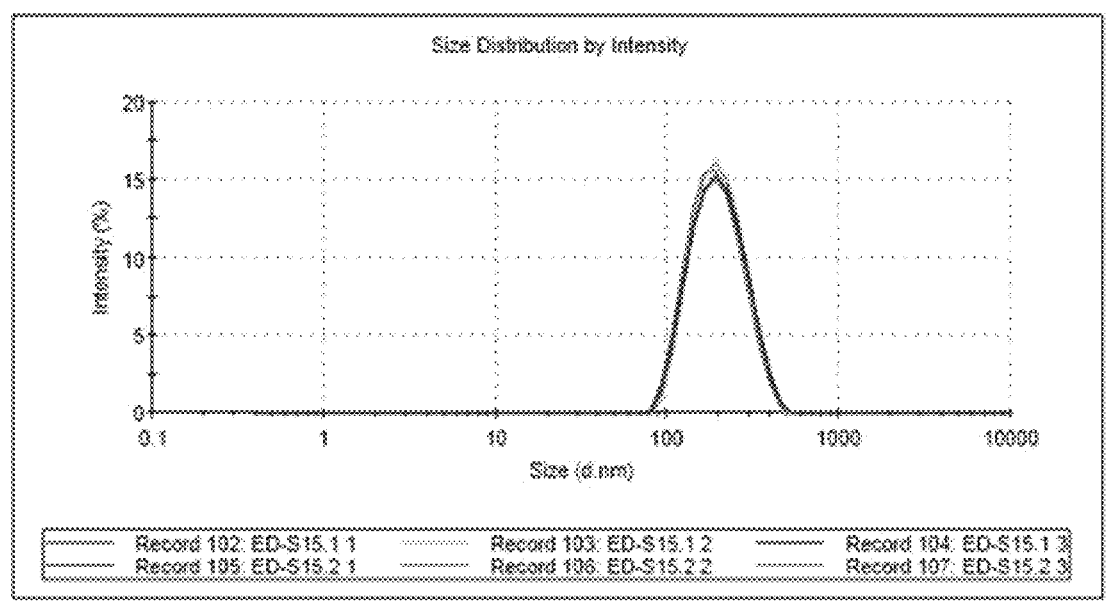

PCT International Preliminary Report on Patentability, PCT/EP2013/069079, dated Mar. 17, 2015.
PCT International Search Report, PCT/EP2013/069079 dated Nov. 21, 2013.
Spinivas et al., Non-emulsion clinical gadolinium/perfluorocarbon nanoparticles for 19F MRI, International Society for Magnetic Resonance in Medicine, May 2012.
Spinivas et al., Customizable multi-functional fluorocarbon nanoparticles for quantitative in vivo imaging using <19>F MRI and optical imaging, Biomaterials, Elsevier Science Publishers BV., Barking, GB, Sep. 1, 2010, pp. 7070-77, vol. 31, No. 27.
Caruthers et al., In vitro demonstration using F-19 magnetic resonance to augment ml=olecular imaging with paramagnetic perfluorocarbon nanoparticles at 1.5 Resla, Investigative Radiology, Mar. 1, 2006, pp. 305-13, Lippincott, Williams & Wilkins US.
Hughes et al., Acoustic characterization in whole blood and plasma of site-targeted nanoparticle ultrasound contrast agent for molecular imaging, J. Acoust. Soc. Am, Feb. 2005, pp. 964-72, vol. 117, No. 2.
Couture et al., A Model for Reflectivity Enhancement Due to Surface Bound Submicrometer Particles, Ultrasound in Med. & Biol., 2006, pp. 1247-55, vol. 32, No. 8, Elsevier.
Sheeran et al., Improving the Performance of Phase-Change Perfluorocarbon Droplets for Medical Ultrasonography: Current Progress, Challenges and Prospects, Scientifica, 24 pages; vol. 2014, Hindawai Publishing Corporation.
Srinivas et al., Non-emulsion clinical gadolinium/perfluorocarbon nanoparticles for 19F MRI, Proc. Intl. Soc. Mag. Reson. Med., 2012, p. 4340, vol. 20.

\* cited by examiner

CONTRAST AGENT AND ITS USE FOR IMAGING

FIELD OF THE INVENTION

The present invention relates to contrast agent enhanced medical imaging. In particular, the contrast agents provided are useful for cell imaging, cell therapy and in vivo targeting and drug delivery applications.

BACKGROUND OF THE INVENTION

Cell therapy is an extremely promising field, which could potentially cure conditions such as diabetes, heart disease and cancer. There are currently over 15,000 ongoing clinical trials involving some form of cell therapy (www.clinicaltrials.gov). A key hurdle in the development and optimisation of cell therapy is that there are insufficient means to monitor the cells once they are in the patient, in a noninvasive manner.

Imaging might provide a clinically applicable solution to monitor therapeutic cells once in the patient, in terms of their viability, localisation, numbers and functionality (see Srinivas M, Aarntzen E H, Bulte J W, Oyen W J, Heerschap A, de Vries I J, Figdor C G. Imaging of cellular therapies. Adv Drug Deliv Rev. 2010 Aug. 30; 62(11):1080-93).

It has been attempted to develop agents suitable for labeling cells so that they could be visualized using a number of imaging techniques, such as 1H MRI, 19F MRI, fluorescence imaging and acoustic imaging techniques, including ultrasound and photoacoustic imaging.

The use of ultrasound in medical imaging procedures is well known in the art. It is the most frequently used clinical imaging modality. Ultrasound is known as an economical, non-invasive, real time technique with a well-established safety record. It can be used for longitudinal studies and repeated use is not harmful for the body. Ultrasound devices do not produce any ionizing radiation and their operation does not involve the use of radiolabels. The devices for performing ultrasound imaging are portable and already in widespread use. Ultrasound imaging is potentially quantitative and it is not a whole body imaging modality, and is therefore limited to target organs. Ultrasound imaging is limited with respect to depth of imaging.

Typically, gas-filled microbubbles are employed as contrast agents in ultrasound imaging. They commonly have a relatively large size (1000-10000 nm diameter) which is generally unsuitable for cell labeling. Moreover, they are also unsuitable to image smaller blood vessels e.g. in tumor imaging. Such gas-filled microbubbles have a short lifetime, typically in the order of seconds to minutes. They also suffer from the additional disadvantage that cell damage may occur as the gas bubbles burst. Moreover, gas-filled microbubbles are unstable so that they cannot be stored for a significant amount of time; they typically have to be used immediately after hydration. Finally, such large agents cannot leave the circulation and thus present very limited opportunities for in vivo targeting or drug delivery applications. Their large size also encourages prompt clearance by the kidneys, which further limits their useful lifetime in vivo.

Ultrasound contrast agents and their use are reviewed in Ultrasound contrast agents: basic principles. Eur J Radiol. 1998 May; 27 Suppl 2:S157-60 and Kiessling et al., Theranostics 2011, volume 1, 127-134.

U.S. Patent application 20100158815 describes the use of contrast agents that are internalized in a cell for improving the ultrasound visibility of the cell. This however has the inherent disadvantage that the agent is gaseous and unstable for cell tracking beyond a few hours.

U.S. patent application 20110020239 provides methods for labeling cells ex vivo for imaging applications, and does not describe in detail any particular contrast agent.

Despite of the many contrast agents that are described to date, there is a great need in the art for stable, affordable and effective contrast agents suitable for cell imaging, preferably with ultrasound and photoacoustic imaging techniques. Both of these would be ideal methods by which to monitor therapeutic cells, if cells could be labeled with a suitable tracer or contrast agent for detection. The technique should preferably be quantitative. Furthermore, stable ultrasound contrast agents would also be applicable to ultrasound angiography, tumor imaging etc.

SUMMARY OF THE INVENTION

We found that the ultrasound and photoacoustic visibility of particles greatly improves when the particle contains a fluorinated organic compound in combination with a metal.

Such particles may be advantageously employed in qualitative or quantitative imaging such as acoustic imaging including photoacoustic and ultrasound imaging, MRI imaging, such as 19F imaging, 1H imaging including T1 and T2 weighted imaging, SPECT, PET, scintigraphy and fluorescence imaging. This may then be employed in cell labeling, microscopy, histology, targeted applications, drug delivery or for imaging vasculature or perfusion in vivo and in vitro.

DETAILED DESCRIPTION OF THE INVENTION

We now herein present improved contrast agents for use in ultrasound and other detection techniques. We herein describe a particle containing a fluorinated organic compound in combination with a metal. We exemplify a poly (lactic-co-glycolic) acid (PLGA) particle comprising a liquid perfluorocarbon and a metal. Such particles were shown to have an improved performance in ultrasound imaging as well as MRI imaging (1H and 19F). The particles may also be detected using fluorescence imaging or bioluminescence if either a fluorescent dye or luciferase (or nucleic acid coding for luciferase) was incorporated in the particle [Pharm Res 2004; 21:354-364].

The term "poly(lactic-co-glycolic) acid" or PLGA is an art recognized term and means a biodegradable polymer of lactic and glycolic acid monomers of variable length and composition. PLGA particles may also comprise addition polymers such as for example poly-ethylene glycol (PEG, Curr Drug Deliv. 2004 October; 1(4):321-33). PLGA particles are known in the art and have been described for use in imaging (for e.g., Biomaterials. 2010 September; 31(27): 7070-7). The structure of PLGA is shown in Formula 1 (x and y denote the number of units of lactic and glycolic acid respectively).

Formula 1

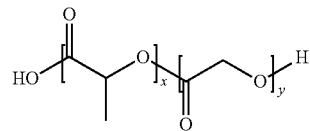

Gas-filled PLGA particles have also been suggested for use in ultrasound. Patent application CN 101574530A describes the use of a PLGA-PEG-PLGA multipolymer microbubble ultrasound contrast agent wherein the microbubble comprises a gas such as perfluoropropane, decafluorobutane or sulphur hexafluoride.

We now found that poly(lactic-co-glycolic) acid (PLGA) particles comprising a liquid fluorinated organic compound is particularly suited for ultrasound and photoacoustic imaging and that the performance of such a particle may be greatly enhanced when a metal is present in the particle.

The term "a" or "an" as used herein refers to at least one. So a fluorinated organic compound is to be interpreted as one or more fluorinated compound.

The term "particle" is used herein in its typical meaning in the art. The term specifically refers to polymer particles that are in solid form when dry at room temperature due to the physical properties of the matrix polymer.

Publications such as Invest Radiol. 2006 March; 41(3): 305-12, Radiology. 2013 August; 268(2):470-80 and several more use the term "perfluorocarbon nanoparticles" to describe "perfluorocarbon emulsion droplets" which are not "particles" as described here. Only one publication, WO2912/113733, lists true particles containing a specific perfluorocarbon and gadolinium agent. However, here the perfluorocarbon acts as an inert carrier and is not an active agent, and the particles are restricted to 1H MRI in hepatocellular carcinoma.

Thus liposomes, micelles and emulsion droplets are not included in the term particles as used herein, as these consist of a liquid surfactant coating (typically a lipid) over the dispersed phase, which is also a liquid. Particles according to the invention do not contain a surfactant and are also stable to repeated freeze/thaw and lyophilization cycles. Emulsion droplets cannot be recovered intact by lyophilization, and emulsions are subject to flocculation, creaming, coalescence and Ostwald ripening. These effects do not apply to particles in a liquid medium, also known as a "sol", which is herein defined as a solid dispersed in a liquid continuous phase.

Furthermore, true particles, like the ones according to the invention can be precipitated, unlike emulsions, which contain a dispersion of minute droplets that cannot be recovered intact by precipitation. Note that emulsion droplets are frequently inappropriately called "particles" or "nanoparticles" in biological literature, although this term is chemically inaccurate.

In addition, the term particle as used herein indicates a small localized object to which can be ascribed several physical or chemical properties such as volume or mass. The particles of the present invention are microparticles or nanoparticles with a size between 1 and 1000 nanometers, preferably between 10 and 1000 nanometers, such as between 50 and 500 nanometers. The size distribution is preferably around a peak between 50-500 nanometers, such as around 100-300 such as 200 nanometers.

In a preferred embodiment, the particles are biodegradable and/or biocompatible.

Several particles together in a solution may form a particulate matter or colloidal suspension or sol, which is also within the scope of the invention. The term particulate matter is used herein to indicate a composition essentially consisting of particles, such as nanoparticles and/or microparticles.

The term "liquid" as used herein refers to the liquid physical state of a compound when in an isolated form at body temperature (37 degrees Celsius) at standard atmospheric pressure (approximately 1000 hectopascal).

The term "fluorinated organic compound" is to be interpreted as an organic compound containing one or more covalently bound carbon and fluorine atoms. A particular useful fluorinated organic compound is for instance a fluorinated organic polymer. In a preferred embodiment, the fluorinated organic compound is a perfluorocarbon.

The term "perfluorocarbon" refers to a carbon compound or polymer where essentially all or all carbon-hydrogen bonds are replaced by carbon-fluorine bonds. Perfluorocarbons can include other elements, such as oxygen. Particularly preferred perfluorocarbons include perfluoropolyethers, perfluoro crown ethers, perfluorooctane and perfluorooctylbromide.

In certain applications as exemplified herein, we advantageously used perfluoro crown ethers. The term "perfluoro crown ether" (PFCE), is to be interpreted as a cyclic perfluorocarbon containing carbon, oxygen and fluorine covalently bound in a stable ring structure. Typically, the PFCE may be a polymer.

A particularly useful perfluoro crown ether is perfluoro-15-crown-5-ether the structure of which is shown in formula 2.

It should be noted that the particles according to the invention are preferably essentially free of surfactant, which means that they contain less than 0.1% surfactant, preferably less than 0.01% surfactant, more preferable less than 0.001% such as less than 0.0001% or 0.00001%. This is also indicated herein as essentially surfactant free. Preferably, the particles do not contain any surfactant at all. This is indicated herein as surfactant free.

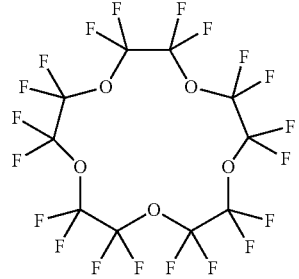

Formula 2

It was found that the performance of the particles comprising the liquid fluorinated polycarbon in ultrasound and photoacoustic imaging could be greatly improved when a metal was included in the particle.

The term "metal" refers to elements defined as metals in the periodic table of elements, including transition metals, alkaline metals and rare earth metals. In particular it refers to metal in biocompatible form, such as metal chelates. A particular favourable metal is gadolinium (Gd). Gadolinium chelates are commercially available such as for example a composition called "Prohance®" comprising gadoteridol. The structure of gadoteridol is shown in formula 3.

Hence, the invention relates to a particle that is essentially free of surfactant, preferably surfactant-free, comprising a perfluoro crown ether and a gadolinium chelate. A particularly preferred particle is a particle consisting of a polymer, more specifically a PLGA particle.

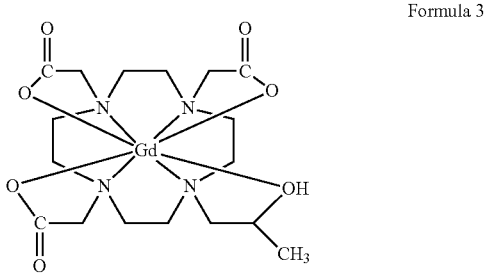

Formula 3

PLGA particles may be synthesized in a broad size range. Advantageously, the particles have dimensions such that cell labeling is feasible, particularly advantageous size distributions include 100-300 nanometers, such as 150-250 nm, such as around 200 nanometers. The term "around" or "about" in this context means plus or minus 10%. This size range is particularly advantageous for extravasation from small blood vessels for in vivo targeting applications.

Particles according to the invention were found to be suited for in situ or in vivo cell labeling, and for that purpose they advantageously contain a targeting agent.

The term "targeting agent" refers herein to an agent that directs the particles to a relevant site or to a particular cell or cell type in vivo or in vitro. Particular advantageous targeting agents include antibodies and receptor ligands.

The particles may also be detected by other methods than ultrasound. The particles can be detected using photoacoustic imaging, without the addition of fluorescent dyes or other agents. Surprisingly, we have found that the PLGA particles with PFCE are detectable using photoacoustic imaging, with the signal enhanced by the addition of metal, such as gadolinium. Peak absorption occurs around 706 nm. The addition of dyes or photoacoustic contrast agents, such as IC-Green® is possible; these can be selected to absorb at the same or different peak frequency as the PFC in the PLGA particles. We also found that the particles can be detected in vivo, for example after intramuscular injection in mice. Cells labeled with the particles can also be detected using photoacoustic imaging, both in vivo and in in vitro phantoms. The PLGA particles containing PFCE are sufficient for detection using photoacoustic imaging, both in vitro and in vivo; and this effect is enhanced by the addition of metals. An example of a suitable particle is a PLGA particle of around 200 nm diameter containing PFCE and gadoteridol.

We found that the particles were also suitable for MRI imaging. "MRI imaging" in this respect means magnetic resonance imaging and includes 1H and multinuclear imaging such as 19F imaging. Furthermore, the imaging can be T1, T2 or proton density weighted.

Particles according to the invention may also comprise a dye, such as a fluorescent dye or a fluorescent protein or nucleic acid coding for a fluorescent agent. That allows for the fluorescence imaging of the particles, including in vivo, as well as histological or other microscopic analyses.

Other ways of detecting the particles is by incorporating a radionuclide in the particle. That allows for autoradiography, scintigraphy, SPECT, PET or other detection methods that can detect radioactive compounds. Also, by incorporating the luciferase enzyme or nucleic acid vector coding for luciferase (or related enzymes), bioluminescence can be used for detection in vivo.

The particles can also be detected using optical coherence techniques, including optical coherence tomography.

LEGEND TO THE FIGURES

FIG. 1: Graph showing the particle diameter distribution for PLGA particles with PFCE, Gadolinium and IC-Geen®. Average diameter was 181 nm. The plot shows the distribution of particle diameters for 6 independent measurements. The close overlap indicates high reproducibility.

Figure 2:
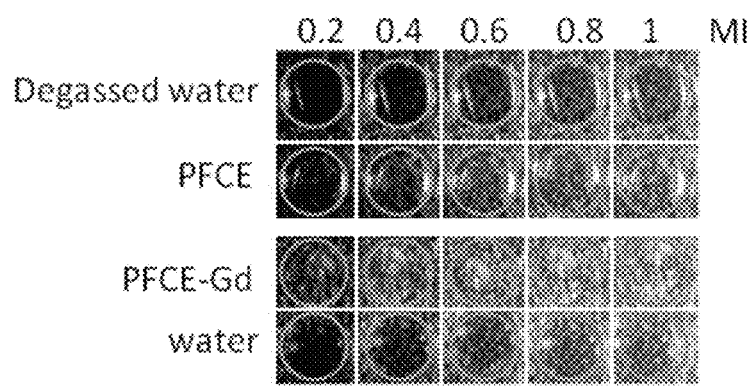

FIG. 2: Image of particles in gel at increasing MI values. The ultrasound images are shown of degassed water (water with the air removed, as a negative control), PLGA particle comprising PFCE (perfluoro-15-crown-5-ether) or PFCE plus Gadolinium (PFCE-Gd) and normal tap water (which has dissolved air and appears brighter). The interpretation of the image is provided as a table below the image wherein + indicates a positive signal and − a negative signal as compared to the degassed water control.

Figure 3:
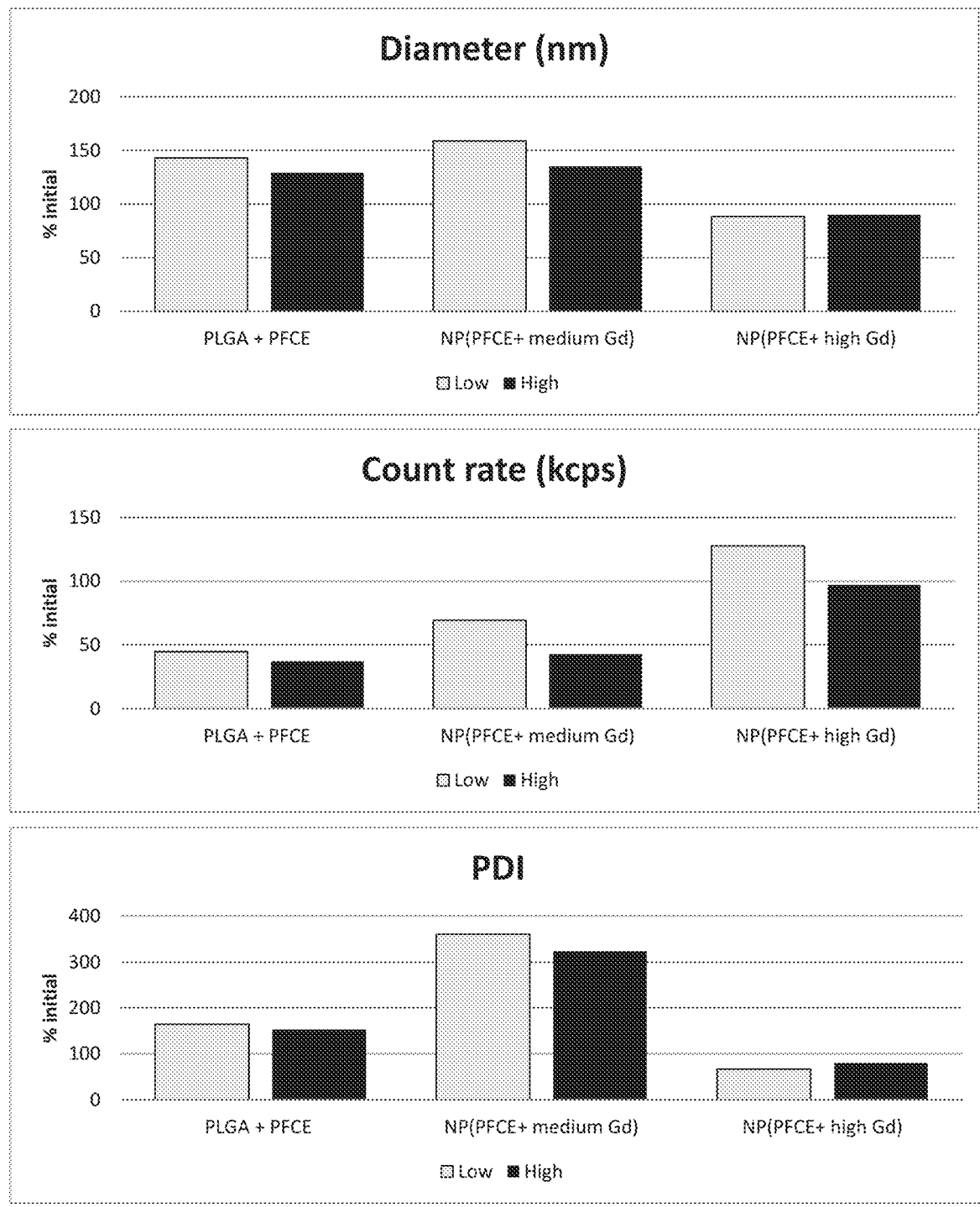

FIG. 3: Diagrams showing the change in the diameter, count rate or PDI (poly dispersity index, indicative of the spread of diameter distribution) after exposure to high (MI=2.0, dark) and low energy (MI=0.1, light grey) ultrasound for 30 seconds. PLGA particles comprising PFCE, with a high and low gadolinium content (example 1) were used and compared to PLGA particles without gadolinium. The graphs are plotted as a percentage of the initial particle diameter after exposure to low and high ultrasound energy. Initial particle diameter was 180 nm. The slight changes after ultrasound exposure are within an acceptable range for cell labeling and other applications.

Figure 4:
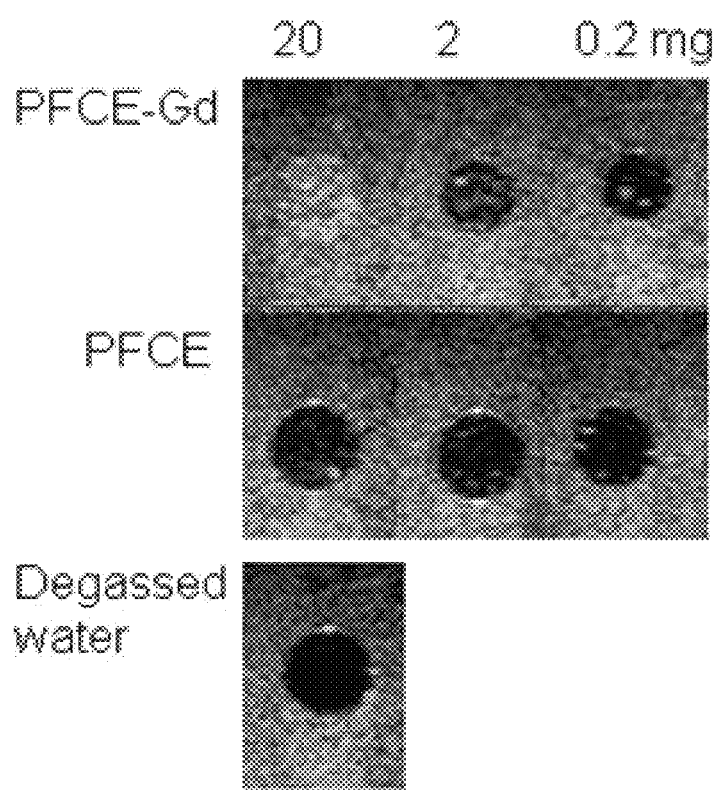

FIG. 4: Images showing the effect of concentration of particles on contrast. Particles were exposed to low energy (MI=0.2) ultrasound in wells in an agarose gel. It is shown that PLGA particles containing PFCE and gadolinium were readily visible at 20 mg per ml whereas concentrations of 2 and 0.2 mg per ml were less visible. PFCE indicates wells with particles comprising PLGA particles comprising PFCE without a metal added. Images were taken immediately after particle addition to prevent settling or coagulation of particles at the bottom of the well. The data indicate a relationship between particle concentration and image contrast which can be exploited for quantification.

Figure 5:
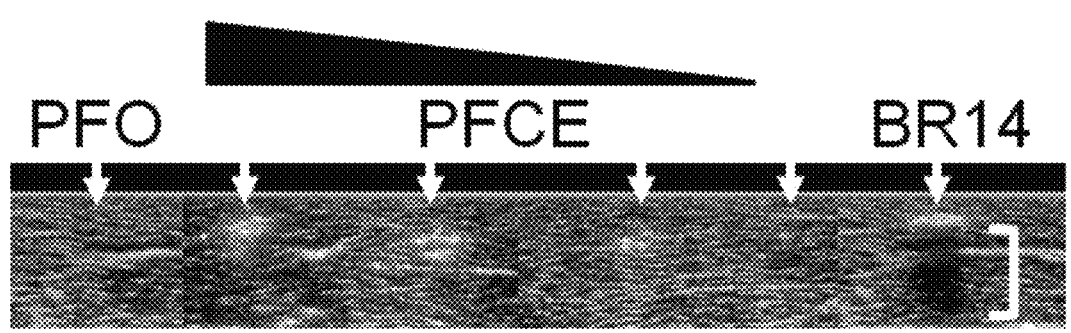

FIG. 5: Image of ex vivo experiments performed with particles according to the invention and a prior art control. Particles according to the invention were injected in liver tissue and visualized with ultrasound (MI=0.2). Images were taken immediately after injection. Images taken after 5 minutes did not indicate any changes. Particles of PFCE with different amounts of Gd added during synthesis (high, medium and low, example 1) were employed, together with BR14 particles. BR14 is a commercial microbubble contrast agent. The injection regions are indicated by the boxes.

Figure 6:
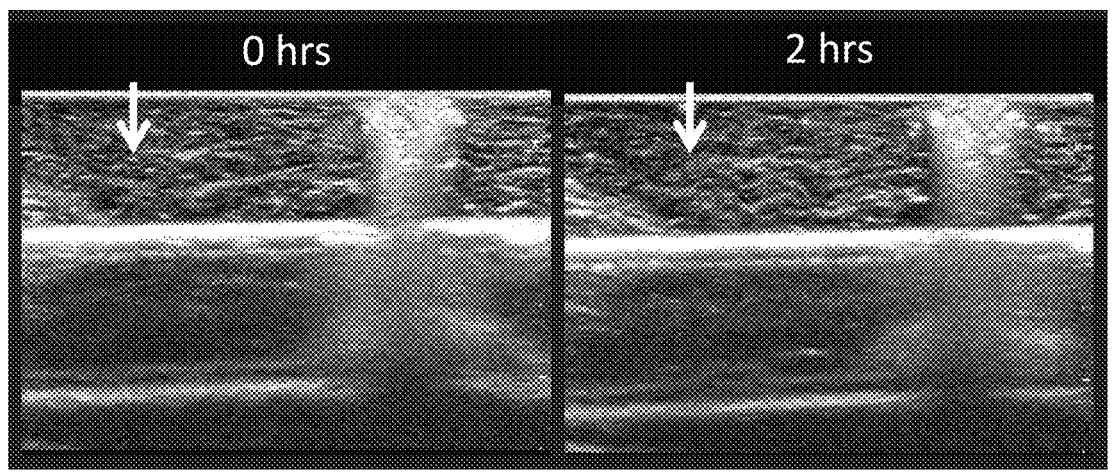
Figure 7A:
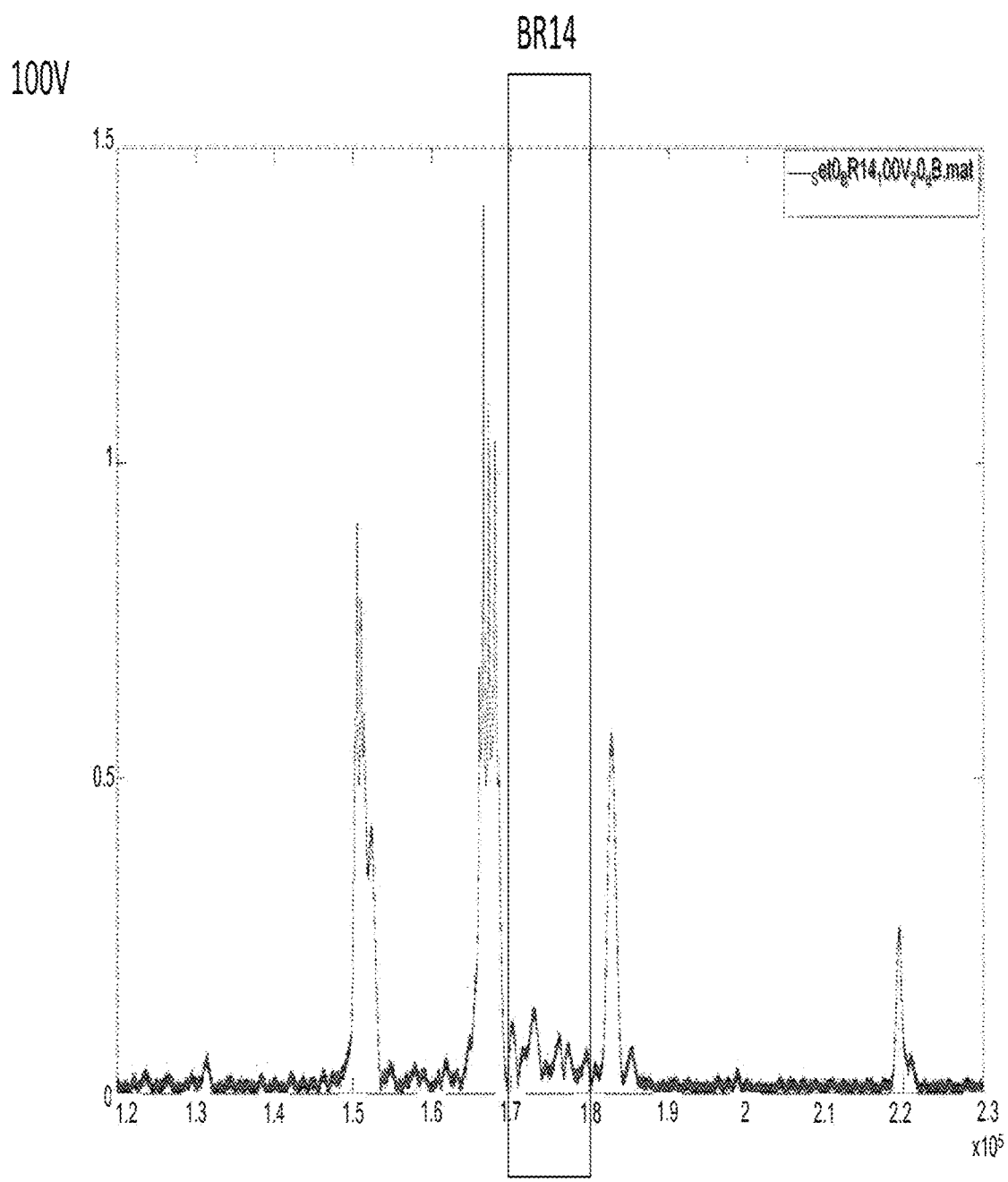
Figure 7B:
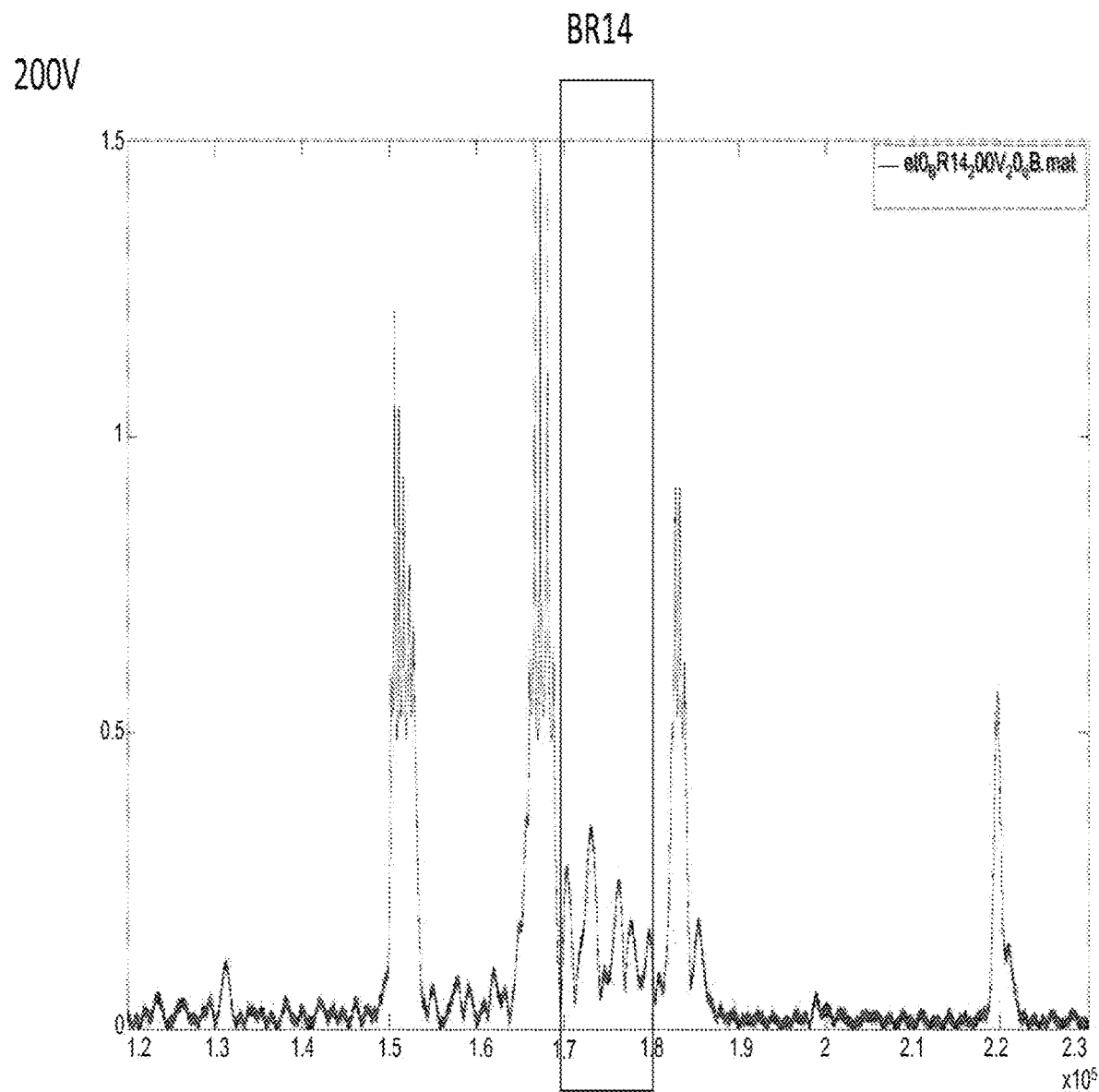
Figure 7C:
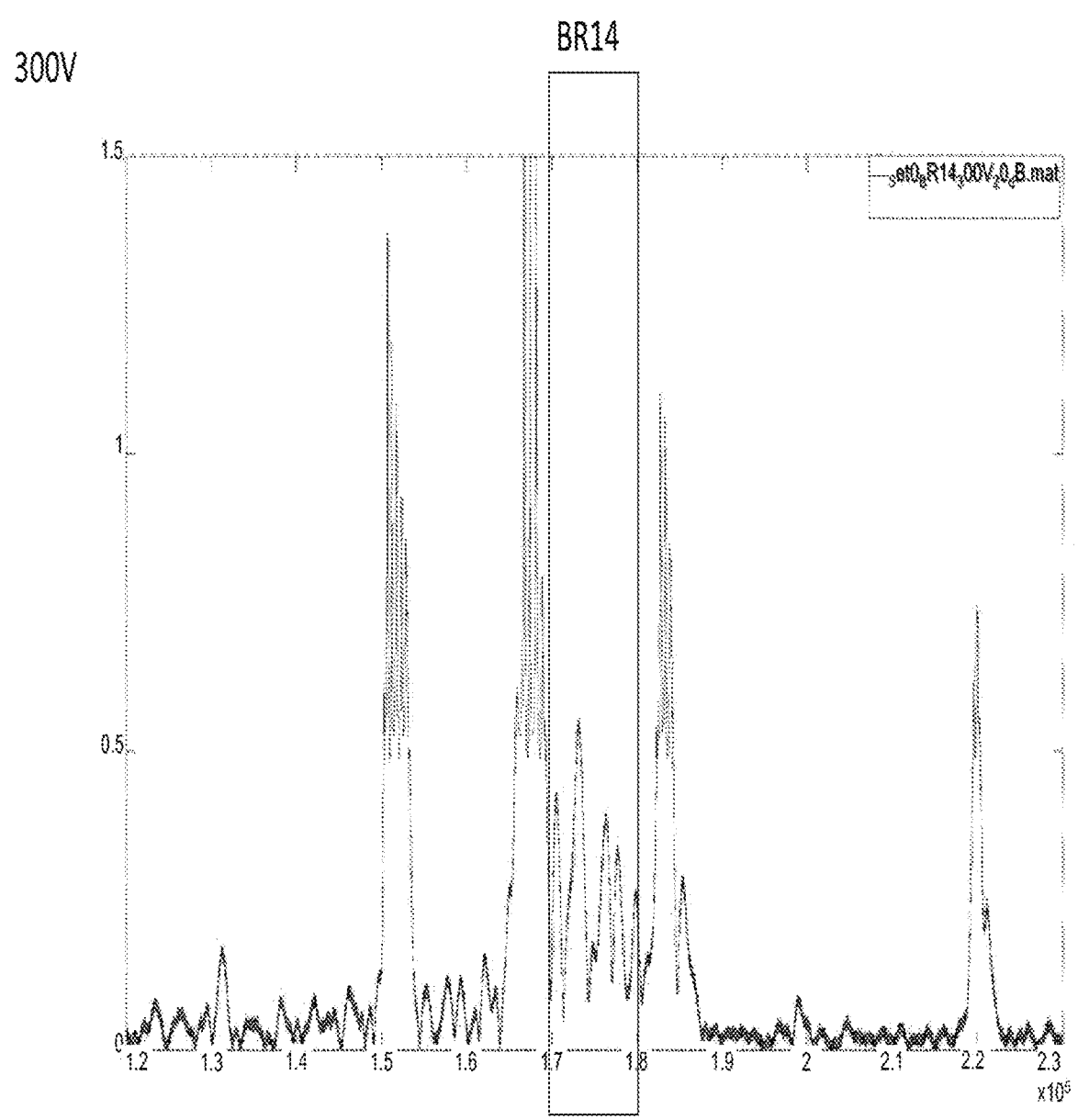
Figure 7D:
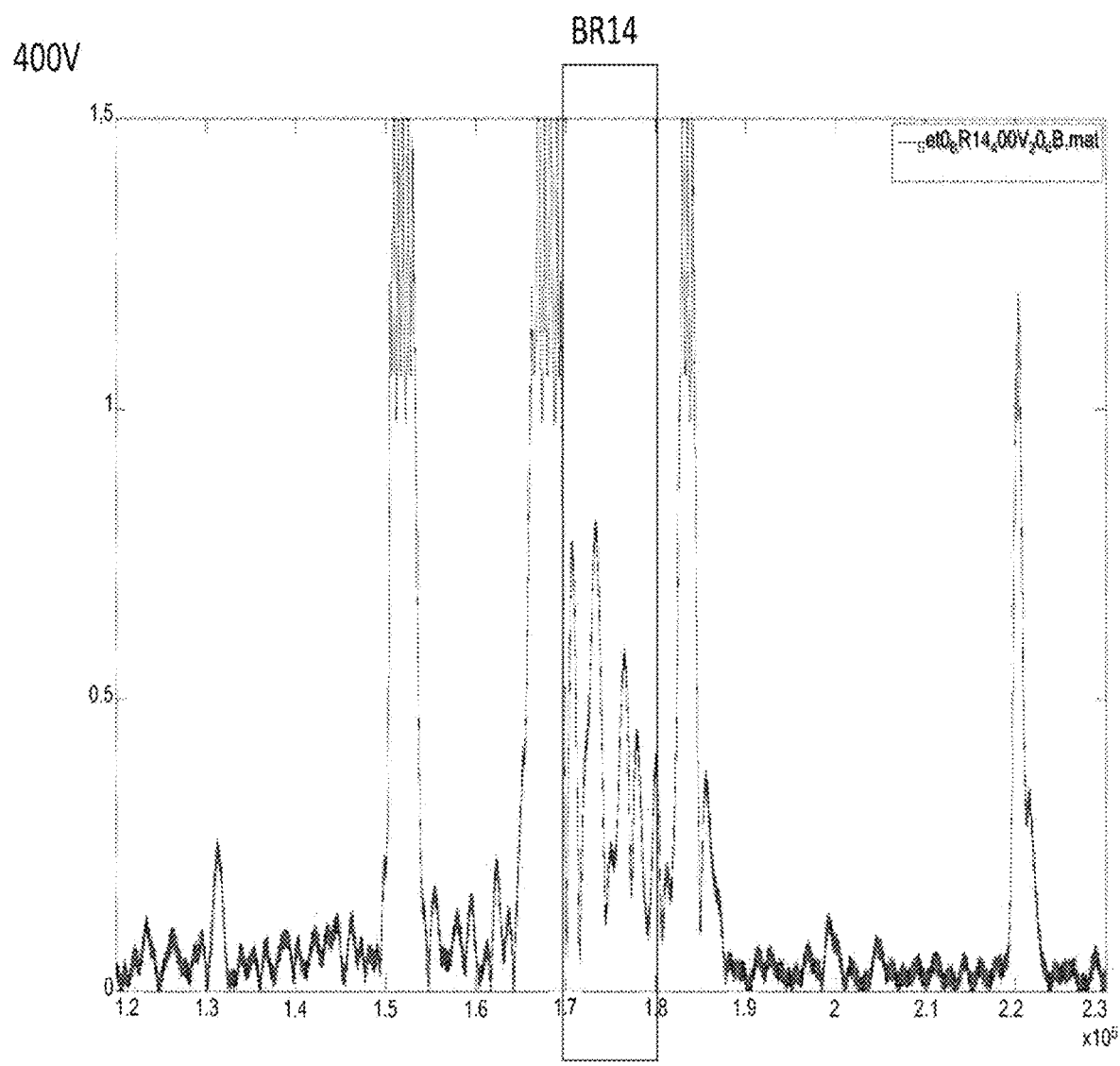
Figure 8A:
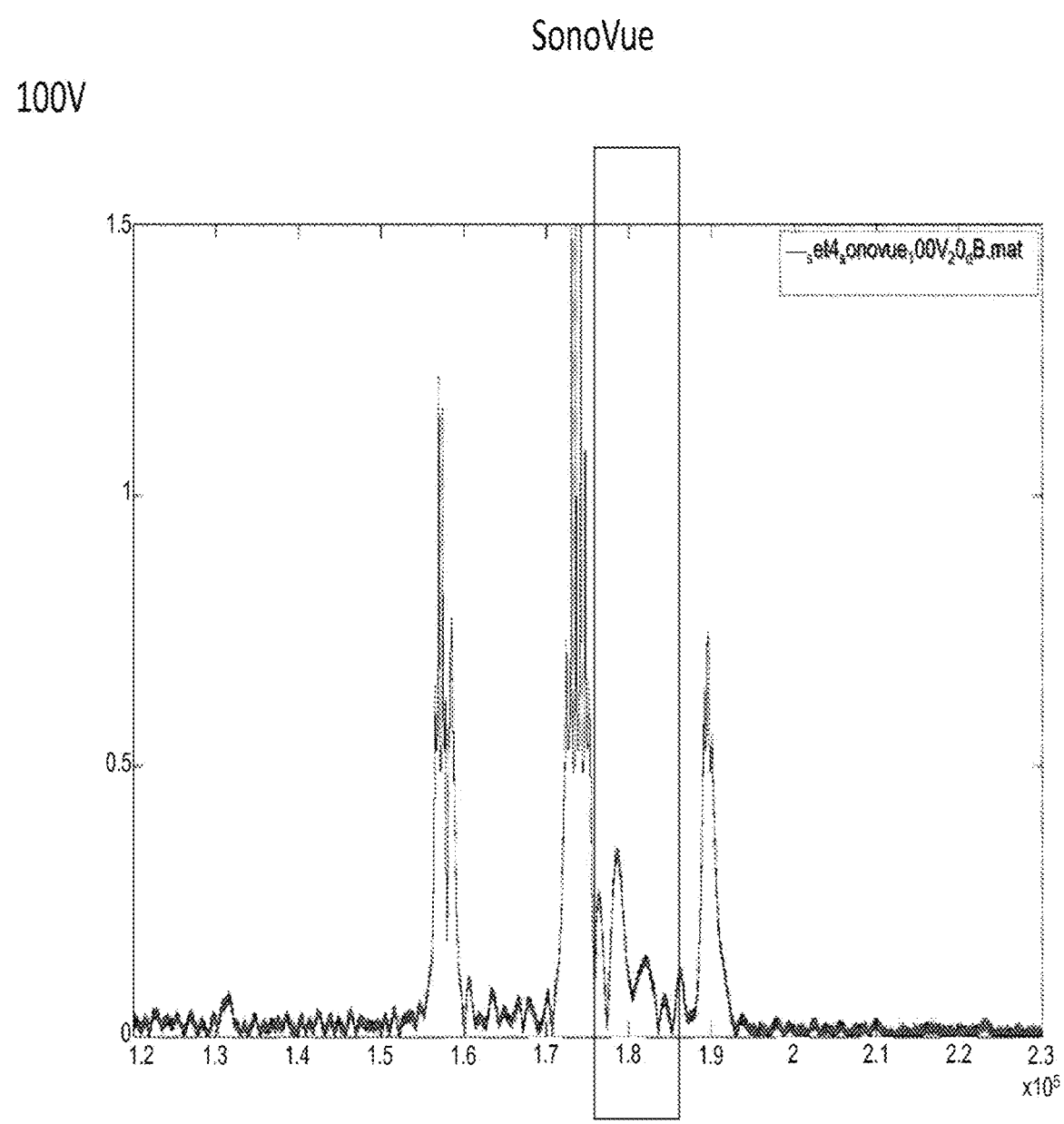
Figure 8B:
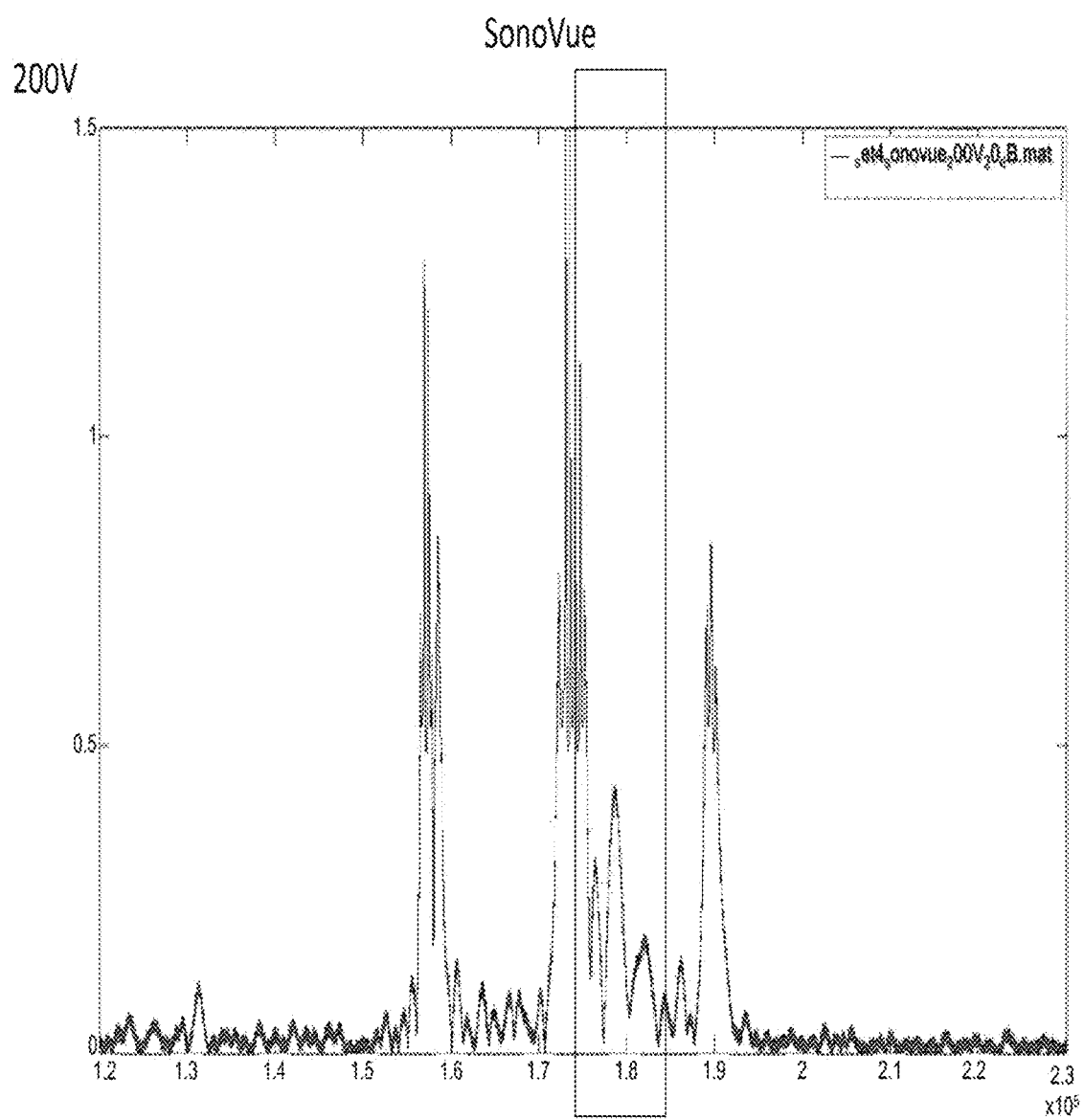
Figure 8C:
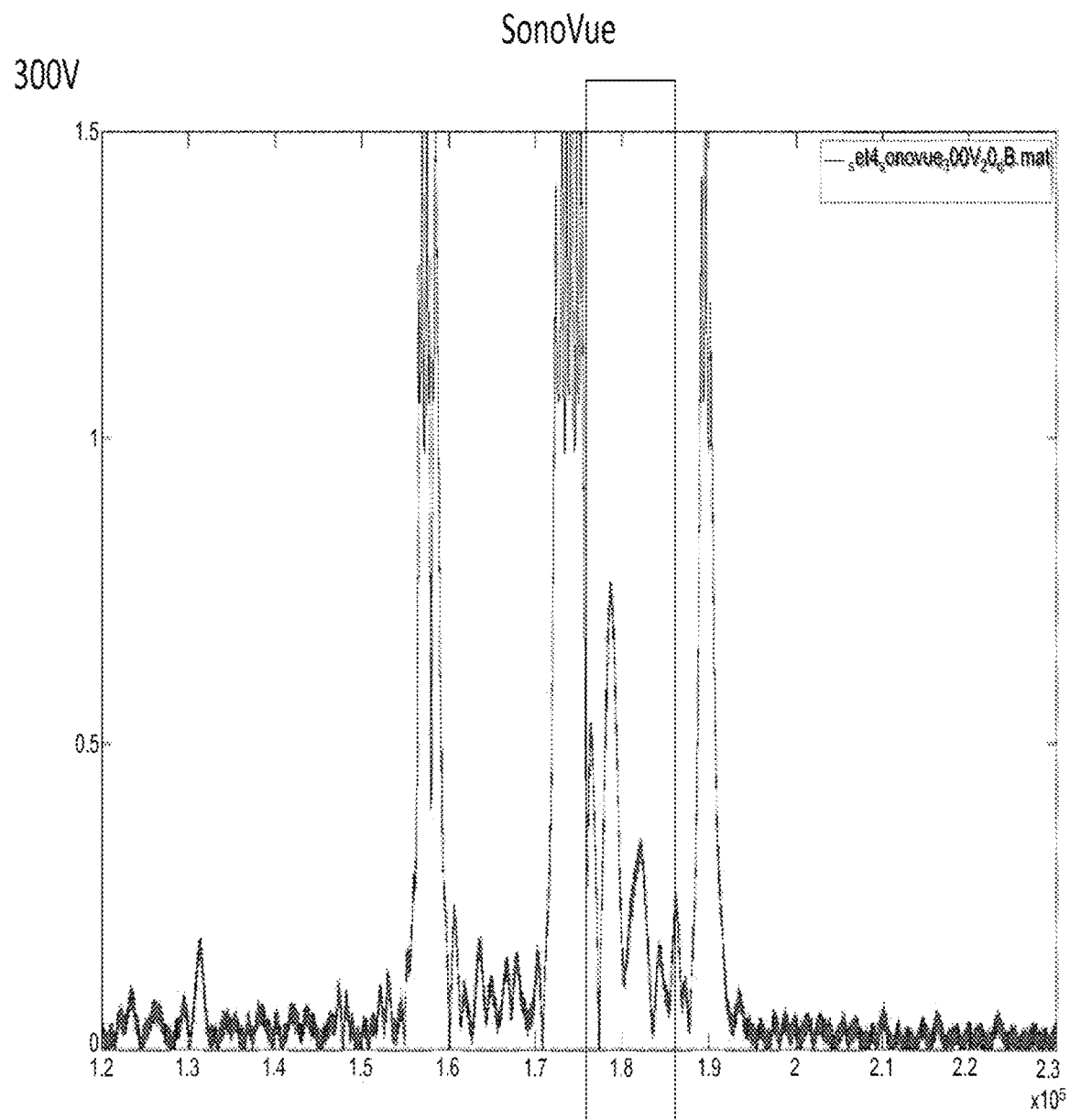
Figure 8D:
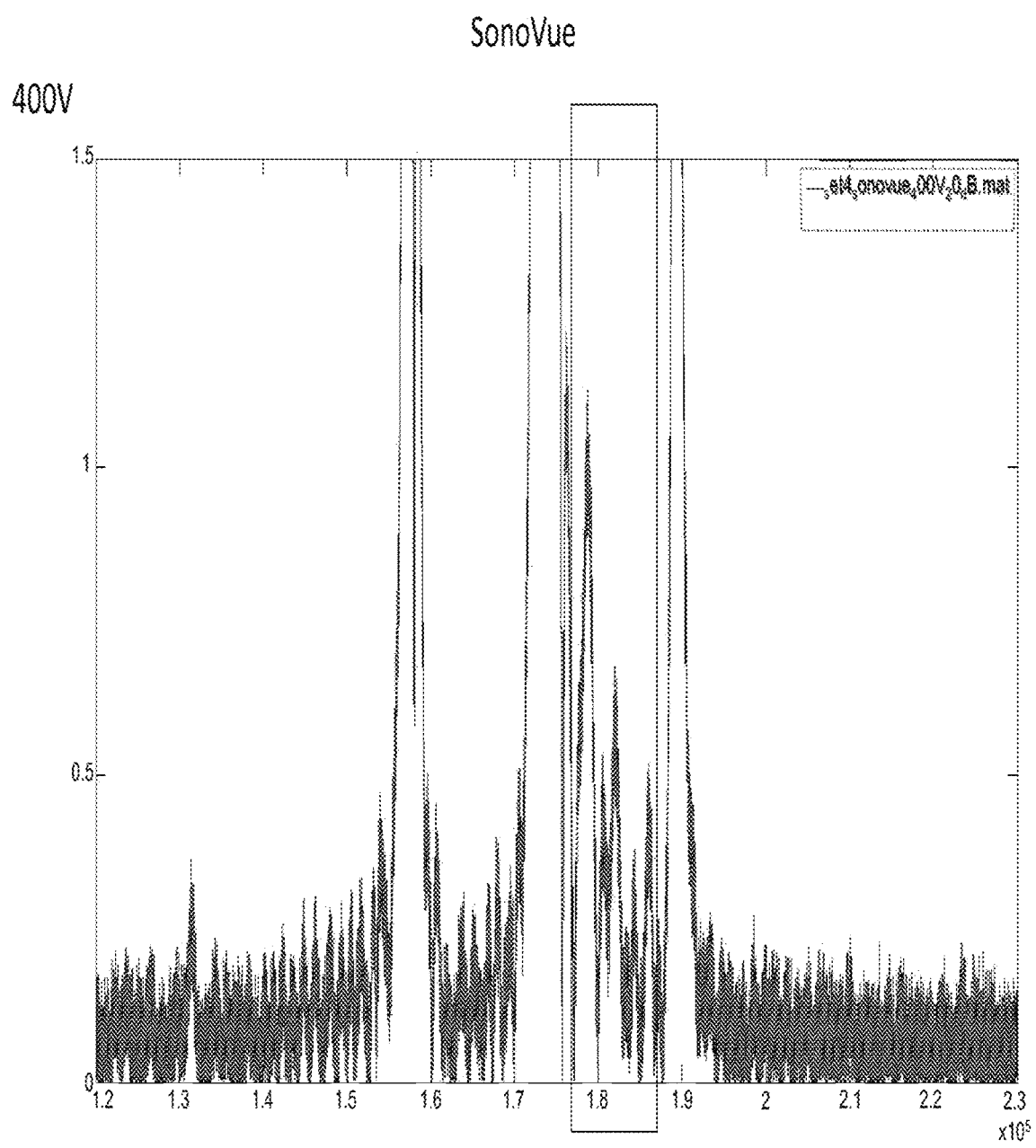
Figure 9A:
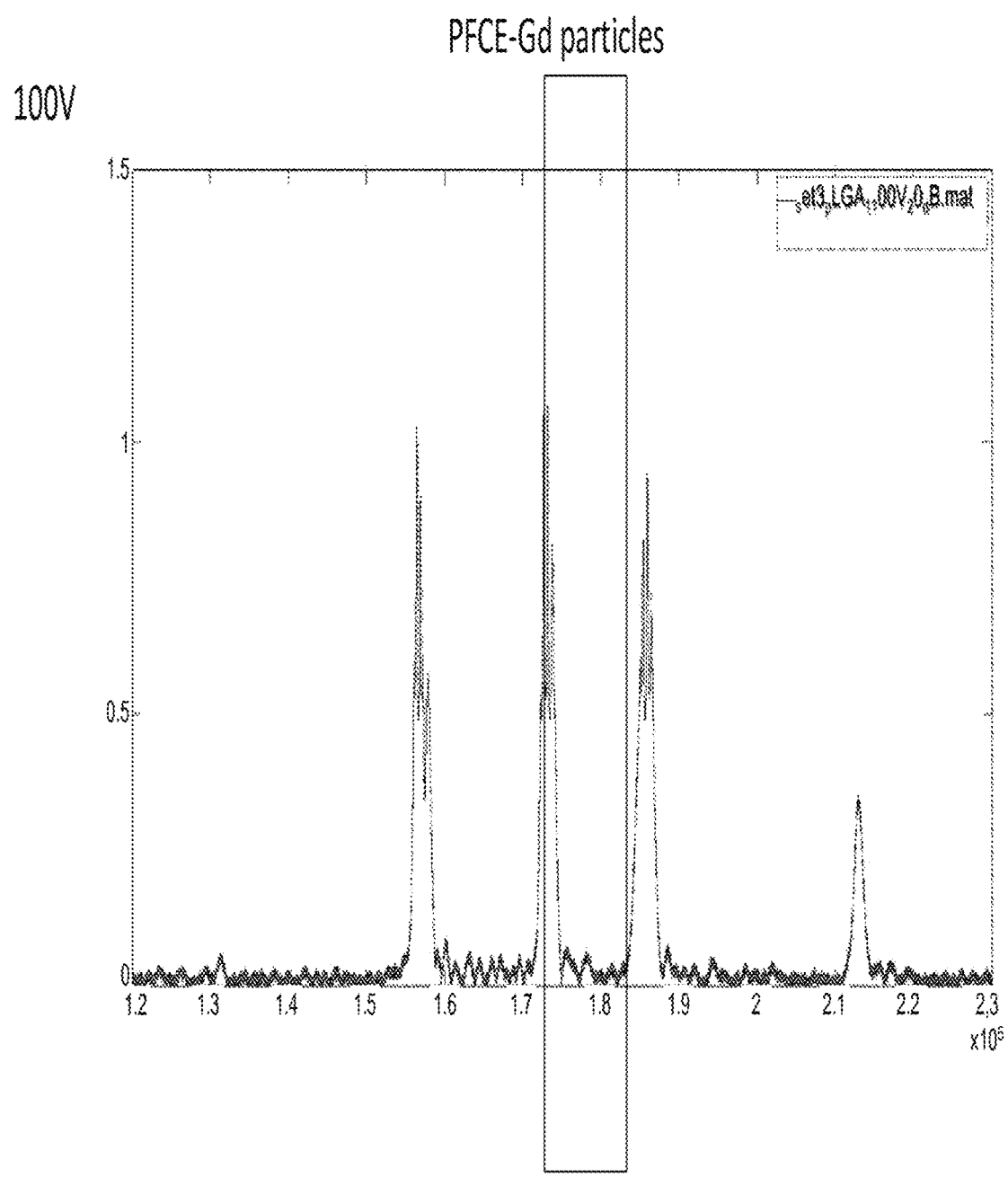
Figure 9B:
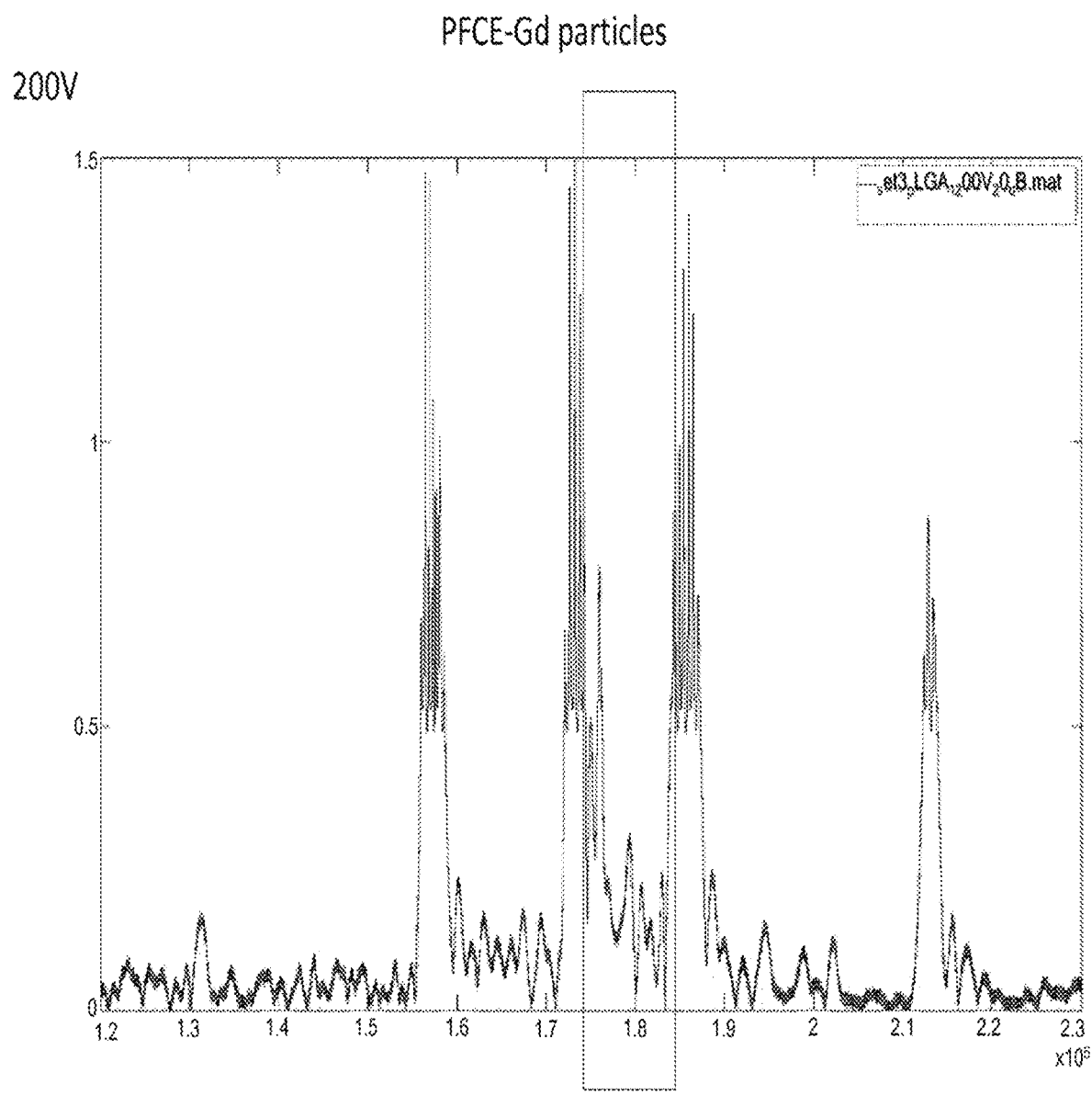
Figure 9C:
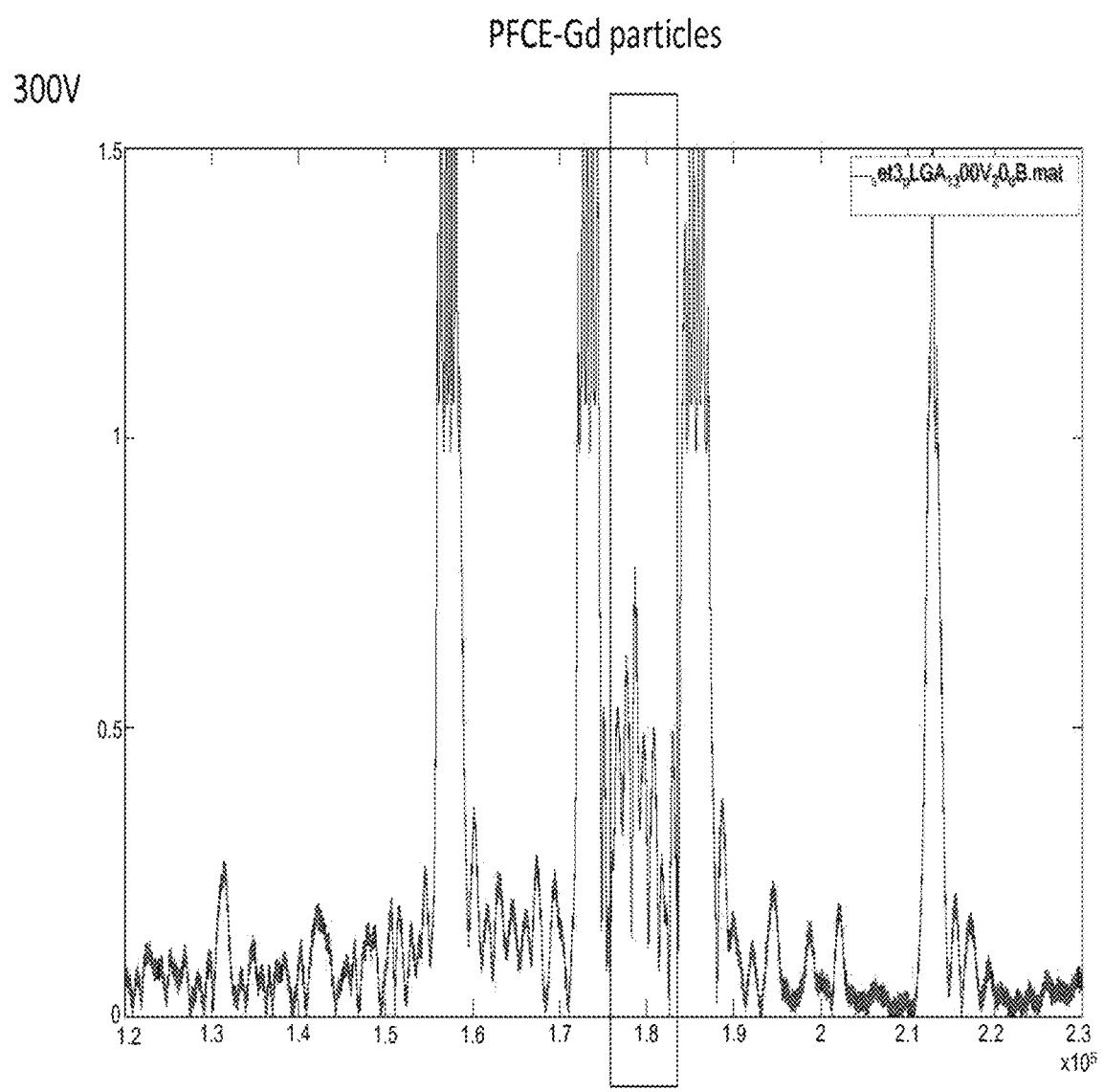
Figure 9D:
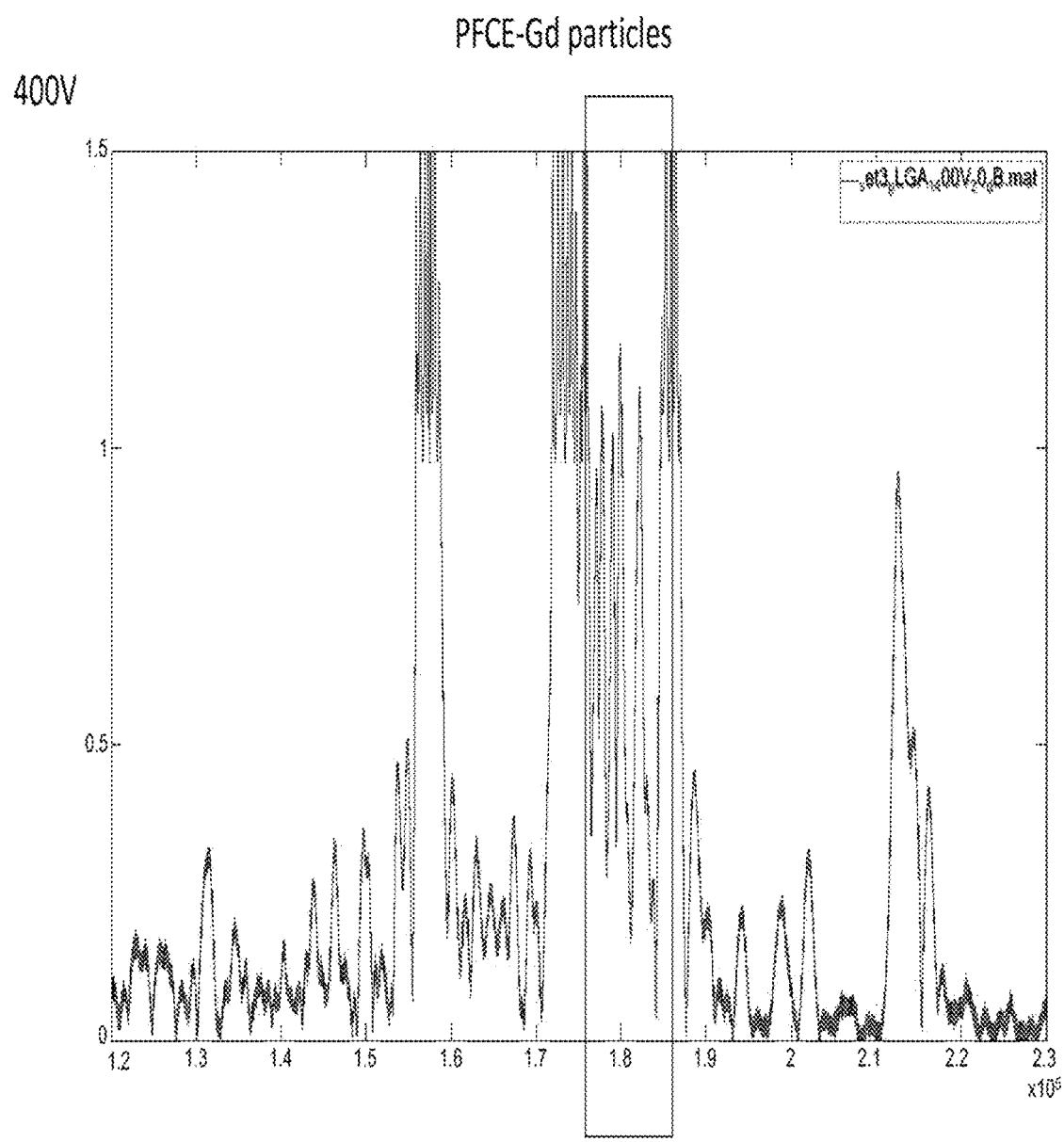

FIG. 6: Images of ex vivo experiments employing particles according to the invention. PLGA particles with PFCE and high Gd content were essentially prepared as described in example 1. Liver tissue was injected with 200 microliter of degassed water (arrow) or 200 microliter of water containing 5 mg of particles. Images were acquired immediately after injection (left panel) and after 2 hours at room temperature (right panel). Contrast from the particles is clearly visible and showed no change over time.

FIGS. 7A-7D: Graphs showing A-mode ultrasound characterization of BR14 microbubbles as described in example 10 at 100V (FIG. 7 (1 of 4)), 200V (FIG. 7 (2 of 4)), 300V (FIGS. 7 (3 of 4)), and 400V (FIG. 7 (4 of 4)). The boxes indicate the relevant region over the sample. Signal within these boxes (i.e. peaks) indicate that the sample is ultrasound-active.

FIGS. 8A-8D: Graphs showing the A-mode characterization of Sonovue® microbubbles as described in example 10 at 100V (FIG. 8 (1 of 4)), 200V (FIG. 8 (2 of 4)), 300V (FIGS. 8 (3 of 4)), and 400V (FIG. 8 (4 of 4)). Sonovue® is a commercial ultrasound microbubble contrast agent sold for clinical use. The boxes indicate the relevant region over the sample. Signal within these boxes (i.e. peaks) indicate that the sample is ultrasound-active.

FIGS. 9A-9D: Graphs showing the A-mode characterization of particles according to the invention as described in example 10 at 100V (FIG. 9 (1 of 4)), 200V (FIG. 9 (2 of 4)), 300V (FIGS. 9 (3 of 4)), and 400V (FIG. 9 (4 of 4)). The boxes indicate the relevant region over the sample. Signal within these boxes (i.e. peaks) indicate that the sample is ultrasound-active.

Figure 10:
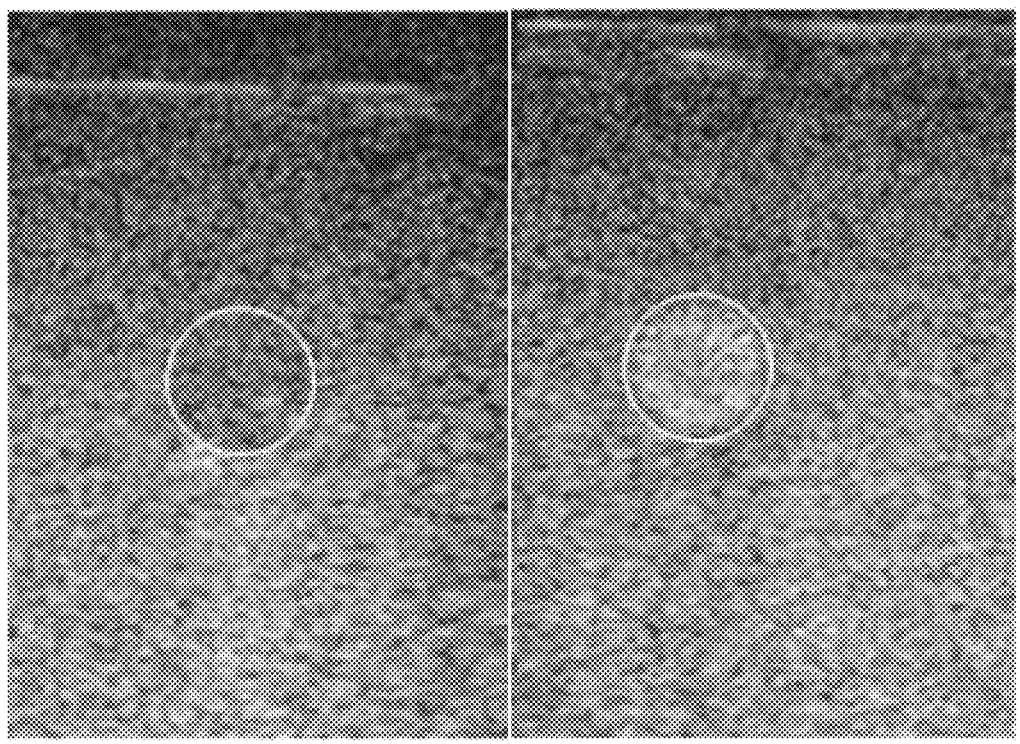

FIG. 10: Image showing the labeling of cells with particles according to the invention. Dendritic cells were labeled with PLGA particles according to the invention as described in example 11. The cells were either not labeled (left panel) or labeled with PLGA particles comprising PFCE and gadolinium (right panel) The PFCE-Gd labeled cells are clearly visible. Non-labeled cells are not visible over background. Circles indicate the region with the cells.

Figure 11:
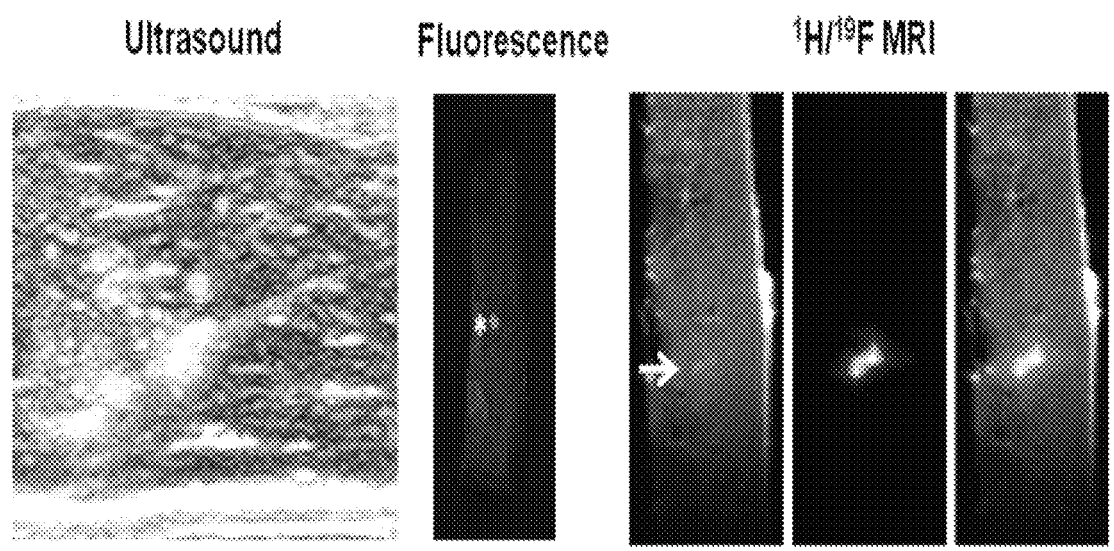

FIG. 11: Image showing that particles according to the invention are suitable for multimodal cell imaging. Two million primary human dendritic cells labelled with PLGA particles comprising PFCE, high gadolinium and IcG could be visualized using ultrasound (left panel) fluorescence imaging (second panel) and magnetic resonance imaging (MRI, third, fourth and fifth panel). The fluorescence images were edited to show the fluorescent region in grey-scale pictures. The three MRI panels show (left) a T1-weighted 1H MRI image (hyperintense region with the cells is indicated by the arrow, (center) a 19F MR image where only the labeled cells are visible and (right) an overlay of the 19F scan over the 1H scan.

Figure 12:
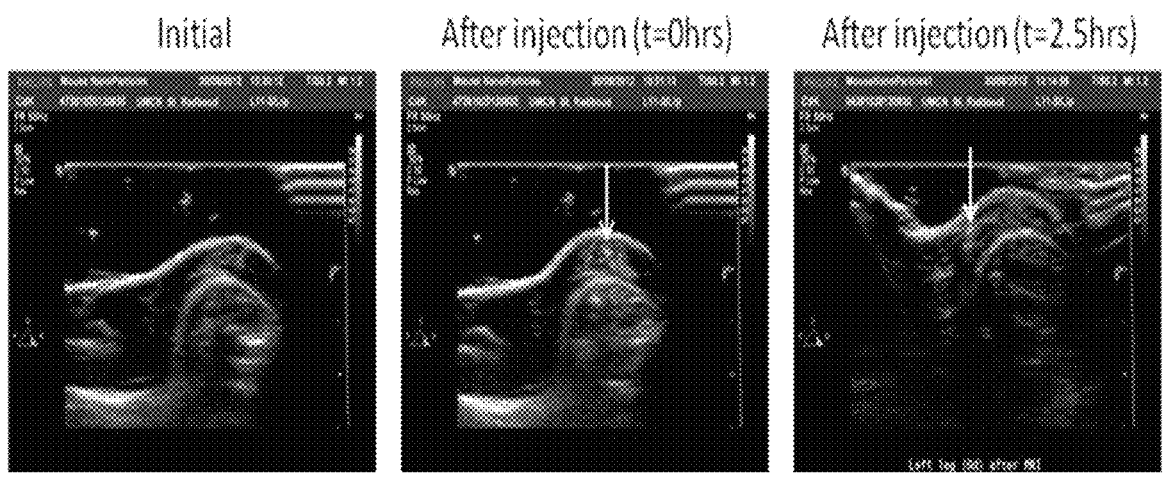

FIG. 12: Ultrasound images of a mouse leg before and after injection of 5 mg of particles according to the invention in the quadriceps muscle. The panel shows images taken immediately before and after injection as well as 2.5 hours after injection. The arrow indicates contrast enhancement due to the particles, detectable both immediately after injection as well as 2.5 hrs later.

FIG. 13: (A) A cartoon representation of the particles is shown for particles of around 200 nm in diameter containing perfluoro-15-crown-5-ether (PFCE) as the PFC, IC-Green® as a fluorescent dye and gadoteridol (Prohance®, Bracco) within the PLGA polymer. (B) 10 mg of various PFCs were tested for acoustic contrast at different MI values ranging from 0.2-1. Degassed water was used as a negative control, followed by particles of empty PLGA (no PFC) and particles with various PFCs, namely PFhexane, PFdecalin, PFO and PFCE. The addition of Gd to the PFCE particles further enhances signal. The particles were imaged in wells in a gel phantom. (C) 10 mg of PLGA particles containing PFO, or PFCE with decreasing concentrations of Gd were injected in pig liver and imaged. 200 ul of BR14 was injected as a control. The region of attenuation that occurs under BR14 is indicated with; this is absent from all the particles. (D) 0.2, 2 and 20 mg of particles containing PFCE, PFCE-Gd, PFO-Gd and PFO only were imaged in a gel phantom. Degassed water was imaged similarly as a control. The signal intensities in the wells resulting from the particles are plotted, showing a linear relationship between particle concentration and acoustic contrast, and that the PFCE-Gd particles result in much higher contrast. (E) Ultrasound images of 2.5, 5 and 20 mg of PFCE-Gd particles injected in liver tissue in 100 ul. (F) EDX (electron microscopy with X-ray diffraction) images showing the localization of IC-Green, PFCE and Gd (from left to right respectively) overlaid on the corresponding electron microscopy (EM) image. The PFCE and dye localize to the outer edge of the particle, while the Gd chelate is internal. The scale bar indicates 200 nm.

FIG. 14: (A) The 19F content of the particles was also measured after insonation. The particles were exposed to 60 seconds of ultrasound excitation at an MI of 1.3 (7.5 MHz scanner, focus at 0.5 cm). (B (1, 2, and 3 of 3)) DLS data was acquired before and after particles were exposed to ultrasound, as previously. The mean particle diameter (nm) (FIG. 14B (1 of 3)), mean count rate (kcps) (FIG. 14B (2 of 3)), and PDI (FIG. 14B (3 of 3)) are shown. (C) Droplet diameter distributions for particles before and after exposure to ultrasound energy. (D) SEM images were acquired on particles before (left) and after probe sonication. No changes were observed in the particles. The scale bar indicates 500 nm.

FIG. 15: (A) Behaviour of different particles irradiated by an ultrasound wave of increasing energy. The results are normalized to the response of tap water and show that for the Sonovue (Bracco) microbubbles the response rapidly collapses as the pressure increases. In contrast, the particles show an increasing response, demonstrating their stability at high ultrasound pressures. Particles with higher Gd content (PFCE-Gdhi) perform the best. Liquid PFCE was used as a control. (B) Schematic of the setup from side and top. A dispersion of the particles is flushed and stabilized in a square glass capillary, and a piezo material is used to create a standing wave in the microchannel, which focuses the particles at the pressure node or antinodes. The lower panel depicts the focusing effect on the particles in time from left to right. In the actual experiment, the particles are standing in the channel and focused at the same moment in the whole channel. (C) Examples of post-processed images for a sample of PFCE-Gd particles (left) and PFOB particles (right). PFCE particles move toward the pressure node located in the middle of the channel whereas the PFOB move toward the pressure antinodes located at the side of the channels. (D) A scattering cross section of various particles calculated using the rigid sphere theory compared to the scattering cross section of a coated bubble, as a function of the size of the particles. A square symbol denotes a positive sign for the radiation force, which translate into a motion directed toward the centre of the capillary, while circles denote a negative sign for the radiation force.

Figure 16A:
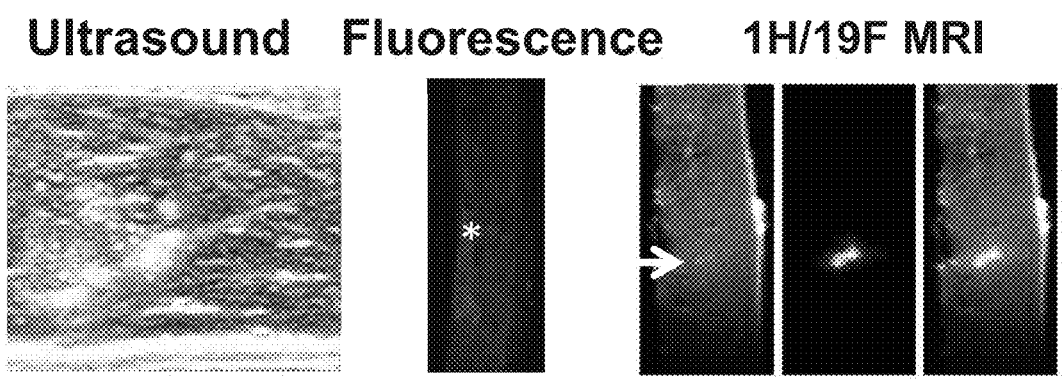

FIG. 16: (A) Fluorescence, 1H and 19F (false color) MRI and ultrasound imaging of 2 million DCs labeled with particles containing PFCE,IC-Green and Gd. The cells were injected in an ex vivo liver tissue sample before imaging. (B) 10 million DCs were labeled with the particles indicated and imaged using ultrasound in wells. (C) 0.2-3 million cells were labeled with particles containing PFCE,Gd and imaged using ultrasound in a gel phantom. The resultant signal intensities for labeled and non-labeled cells are plotted.

FIG. 17: (A) Ultrasound images of the quadriceps muscle of a mouse before, immediately after (0 hrs) and 2.5 hours after injection of 5 mg of PFCE-Gd particles (arrow). The mouse was unrestrained and allowed to move freely after the injection. (B) High frequency ultrasound images of the inguinal lymph node of a mouse before (left) and after (right) injection of 0.1 mg of PFCE-Gd particles. The mean contrast of the node changed from 230 to 2662 arbitrary units after injection. (C) Mice were injected with 20 mg PFCE-Gd particles s.c. and monitored for 2 weeks. The images (from top to bottom) show the kidneys, spleens, livers and draining ipsilateral or control contralateral inguinal lymph nodes of one control and two injected mice. Furthermore, the mice did not show any changes in weight or behavior (not shown).

EXAMPLES

Example 1

Preparation of Particles Comprising Perfluoro-15-Crown-5-Ether

PLGA (0.09 gram) was dissolved in 3 ml dichloromethane in a glass tube. Liquid perfluoro-15-crown-5-ether (890 microliter) was added followed by 50 ml of a solution of Prohance® (a 3 mg/ml solution of gadoteridol) diluted in water. Optionally, additional agents, such as a fluorescent dye, may be added to the fluorocarbon at this stage. If a fluorescent particle was required, 1 mg of IcG or IC-Green (Indocyanine Green, Akorn Pharmaceuticals) was added to the solution.

As detailed herein below, we prepared particles with a high, medium and low content of Gadolinium. For that purpose, the above mentioned solution of Prohance® in water comprised 11.5, 5.75 and 2.85 ml respectively of Prohance® added up with water to 50 ml of solution. The entire mixture was then added dropwise into 25 ml of a solution of polyvinyl alcohol in water (20 gram/liter) under constant sonication (Branson Digital Sonifier 250; 3 minute cycle with 60 sec on and 10 sec off and maximum temperature of 20 degrees Celsius and amplitude of 30%; a cuphorn was used) The resulting emulsion was then placed at 4 degrees Celsius and allowed to evaporate with constant stirring for about 12 hours until 24 ml of solution remained. An equal volume of water was then added and the emulsion was centrifuged at 21000 g for 30 minutes at 4 degrees Celsius. The pellet was washed with water twice and the resultant suspension was lyophilized at −60 degrees Celsius, for at least 24 hours The particles were then placed in sealed tubes and stored at −80 deg Celcius. Unless stated otherwise, the particles used in the experiments described herein are the particles with the highest gadolinium content.

Example 2

Characterisation of Particles

We found that particles as prepared above were stable for at least a year when kept at −20 degrees Celsius in the dry form. The particles were also stable in solution at working concentrations for at least 3 months at minus 4 degrees Celsius.

Diameter of particles prepared according to example 1 was determined using dynamic light scattering (DLS) as previously described (Biomaterials. 2010 September; 31(27):7070-7). FIG. 1 shows that the particle size ranged from 80 to 500 nm with a sharp peak at 181 nm. FIG. 1 shows the results of 6 individual and independent syntheses. The results are identical; all curves essentially overlap, indicating a high reproducibility. The particle diameter distribution remained stable for several months. The particles were lyophilised and frozen for storage. However, particles stored as aliquots in water (frozen) were also stable.

The particles prepared according to example 1 with high and medium gadolinium content, dissolved in water at a concentration of 1 mg/ml appeared to be exceptionally stable under conditions of ultrasound imaging. We measured particle diameter and count rate (indicative of number of particles) before and after exposure to low and high ultrasound MI (MI=0.1 and 2.0) for 30 sec. Count rate indicates roughly the number of particles per sample, and thus whether the particles were destroyed by the ultrasound. The count rate graph indicates that increasing Gd content improves stability of the particles to ultrasound exposure. We found no change in the diameter, count rate or PDI (indicative of the spread of diameter distribution) after exposure to high energy ultrasound for 30 sec (FIG. 3).

It is concluded from the data presented in FIG. 3 that the particles according to the invention are stable under even the harshest ultrasound conditions and that increasing Gd content improves stability of the particles to ultrasound exposure.

Example 3

Ultrasound Imaging In Vitro

A linear array transducer (L11-3) with central frequency 7.5 MHz was used for all the ultrasound scans (SONOS 7500, Philips Medical Systems, Best, The Netherlands). The MI was variable, from 0.1-2.0, as indicated. Gain was typically set to 90%.

Gel phantoms consisted of 8% gelatin (Dr. Oetker, Ede, The Netherlands) and 2% agar (Agar Powder CMN, Boom, Meppel, The Netherlands) solution (these gels showed as bright in the ultrasound images).

Ultrasound exposure was performed at Mechanical Index (MI) ranging from 0.2 to 1. MI is a safety metric indicating how much energy is transferred to the subject or sample during imaging; clinical limits are 1.9 for diagnostic imaging and 1.0 for obstetric scans).

Example 4

Ultrasound Imaging Ex Vivo

A linear array transducer (L11-3) with central frequency 7.5 MHz was used for all the ultrasound scans (SONOS 7500, Philips Medical Systems, Best, The Netherlands). The MI was variable, from 0.1-2.0, as indicated. Gain was typically set to 90%.

Example 5

Ultrasound Imaging In Vivo

A linear array transducer (L11-3) with central frequency 7.5 MHz was used for all the ultrasound scans (SONOS 7500, Philips Medical Systems, Best, The Netherlands). The MI was variable, from 0.1-2.0, as indicated. Gain was typically set to 90%.

Example 6

Gadolinium Improves the Ultrasound Visibility of Particles

PLGA/PFCE particles were prepared according to example 1 with a high Gd content and tested for ultrasound visibility according to the protocol of example 3. The results are shown in FIG. 2. It is shown therein that the addition of gadolinium enhances the ultrasound signal. It is concluded that the addition of gadolinium provides an improvement of the ultrasound visibility of particles comprising a fluorinated organic compound.

Example 7

Quantitation

PLGA/PFCE particles prepared according to example 1 with a high Gd content were tested for ultrasound visibility according to the protocol of example 3. Different concentration of particles were used; 20, 2 and 0.2 mg/ml, diluted in water. The results are shown in FIG. 4. It is shown therein that the ultrasound signal is proportional to the concentration of particles used. It is concluded that the particles according to the invention are useful in quantitative ultrasound imaging. In independent experiments it was confirmed that as little as 200.000 cells could be visualized when labeled with the particles according to the invention.

Example 8

Comparison with Prior Art

PLGA particles containing liquid PFCE and high, medium and low quantities of gadolinium were injected into pig liver and visualized by ultrasound (MI=0.2), essentially according to the protocol of example 4. For comparison, the pig liver was also injected with BR14, a commercially available (Bracco Diagnostics) 3000 nm particle comprising a perfluorobutane gas core.

We observed a quantitative response of the Gd containing particles that was not destroyed upon ultrasound exposure. Quantitative in this respect means that the signal increases upon increasing gadolinium content of the particles. Moreover, the particles according to the invention did not produce a so-called shadow, as is usually obtained with gas-core particles. This shadow effect was notably present underneath the BR14 injection area (FIG. 5). We conclude that the particles according to the invention provide advantageous properties in comparison with the prior art, both on the level of a quantitative response that is not destroyed upon ultrasound exposure as well as the absence of a shadow. The latter allows a much more detailed analysis of the area under investigation.

Example 9

Particles According to the Invention Remain Visible Over Time

Particles prepared according to example 1 (5 mg particles with a high gadolinium content in 200 microliter water) were injected into liver tissue according to the protocol of example 4. Water was injected as a control. The results in FIG. 6 show that the particles were clearly visible in liver tissue even after 2 hours at room temperature. Prior art contrast agents comprising a gaseous core typically have much shorter lifetimes especially upon exposure to ultrasound energy [Phys Med Biol. 2009 Mar. 21; 54(6):R27-57]. We concluded from the data of FIG. 6 that the particles according to the invention provide for a long lasting signal in ultrasound imaging. The absence of a shadow-effect is also noted in this experiment.

Example 10

Head-to-Head Comparison with Prior Art Particles

Samples containing prior art contrast agents were compared to the contrast agents according to the invention. Agents as noted (BR14 in FIGS. 7A-7D, Sonovue in FIGS. 8A-8D and PLGA particles containing PFCE and high gadolinium in FIGS. 9A-9D) were exposed to ultrasound and the resultant echoes are recorded and plotted. A-mode or amplitude mode is a standard ultrasound characterisation technique. The y-axis represents the amplitude of the received signal and the x-axis is time. Echoes are also generated from the walls of the container and other interfaces. The relevant region (containing the sample) is indicated by a box in the images. Data are shown at 4 different voltages (equivalent to different MI values). The plots are shown for BR14 and SonoVue microbubbles (both available commercially) and PLGA/PFCE plus Gd particles, prepared as described in example 1.

All samples were at 5 mg in 200 ul. The samples were placed in holders in a water tank with a 5 MHz focussed transducer (Panametrics NDT A308S, 1.5 inches focal distance). The transducer was connected to a pulse receiver (Squarewave 5066PR) triggered by a delay generator to work in single pulses (BNC delay generator model 575). The output of the receiver was routed to an oscilloscope (Tektronix 4034) set in single mode. The focus was set to the centre of the holder (i.e. to the sample) and the backscattered signal was recorded. The frequency was set to 5-6 MHz (centre frequency of the transducer) and the voltage applied was varied from 100-400V. The data obtained was processed using a Hilbert transform.

The data show that the gadolinium containing particles according to the invention have a comparable if not superior performance compared to the commercial agents. Moreover, the commercial agents were destroyed by the experiment but the particles according to the invention were not.

Example 11

Cell Labeling

We labeled primary human dendritic cells (DCs) with the particles essentially as described in Biomaterials. 2010 September; 31(27):7070-7 and NMR Biomed. 2012 September; 25(9):1095-103. Therein, the labeling of cells is described with PLGA particles comprising fluorinated polycarbons without metal in the core. We found that the additional metal as used in the particles according to the invention had no effect on viability, phenotype, functionality and migratory ability of the cells. Also, cell uptake of the particles is not affected by the metal content of the particle. This is not surprising since only the PLGA is exposed. Furthermore, the actual metal content of the particles is tiny and not expected to affect the cells. The total gadolinium load delivered per million cells is nearly 100-fold lower than the approved clinical dose of gadolinium for in vivo use.

10 million labelled dendritic cells (DC) were imaged by placing them in wells in agarose gel. Here, we imaged the bottom of the well as the cells settle very quickly to the bottom. The results are shown in FIG. 10. We conclude that cells may well be visualized using particles according to the invention in ultrasound imaging.

Example 12

Multimodal Cell Imaging

Cells labeled with particles according to the invention were visualized ex vivo with ultrasound imaging, fluorescence imaging and MRI.

Particles containing a fluorescent dye were prepared according to example 1 and used in multimodal imaging. The results are shown in FIG. 11. It is concluded that the particles according to the invention are visible with ultrasound and MRI (both 1H and 19F) and if containing an additional dye, also in fluorescence imaging. Ultrasound image: The cells are the bright white spots. Fluorescence: The asterisk (*) indicates the cells. The presence of the fluorescent dye, IcG, allows fluorescence imaging). MRI: T1 contrast (arrow) occurs due to the Gd), and 19F signal arises from the PFCE (false colour).

Example 13

Microscopy and Histological Analyses

Particles containing a fluorescent dye were prepared according to example 1 and used in histological analyses, essentially as described in Biomaterials. 2010 September; 31(27):7070-7 and NMR Biomed. 2012 September; 25(9):1095-103. Therein, the labeling of cells is described with PLGA particles comprising fluorinated polycarbons without metal in the core. We found no difference in the intracellular and in vivo behavior of the particles according to the invention and conclude that addition of a fluorescent dye to the particles of the invention allows for intracellular study of the particles, as well as histological analysis after transfer in vivo.

Example 14

In Vivo Imaging

Particles were prepared according to example 1 with a high gadolinium content. Five mg of particles was injected in the quadriceps muscle and ultrasound Images obtained according to the protocol of example 5. FIG. 12 shows the results before injection, immediately after injection and 2.5 hours after injection. It may be concluded from FIG. 12 that the particles are readily visible in vivo and that the contrast due to the particles persists, even after 2.5 hours in vivo.

Example 15

Further Experiments

Figure 13A:
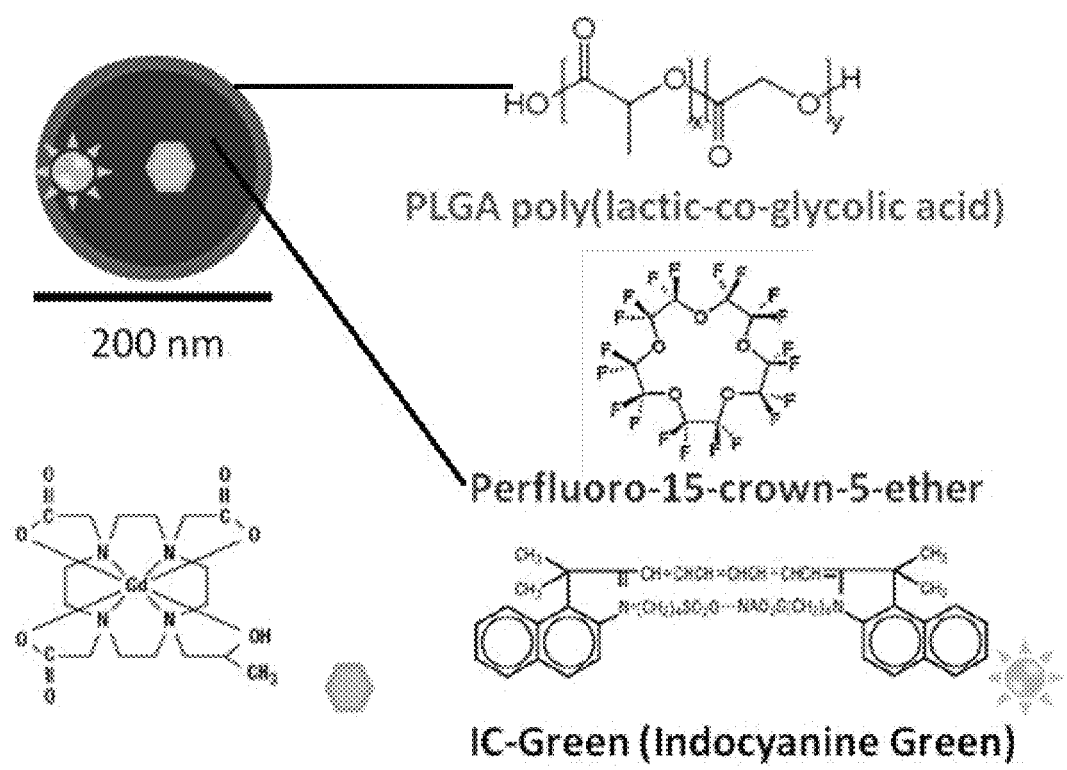
Figure 13B:
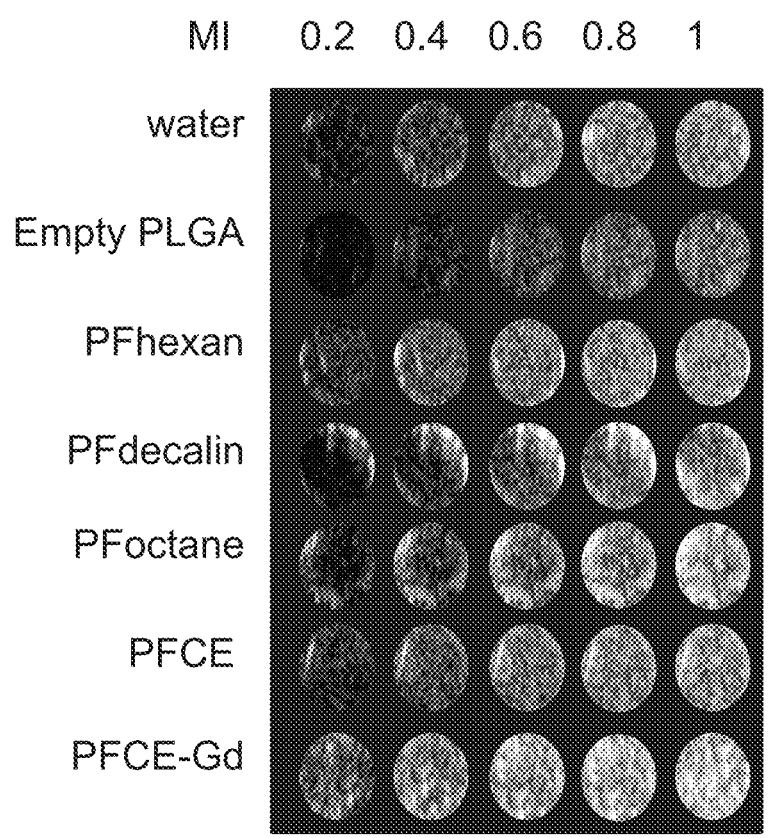
Figure 13C:
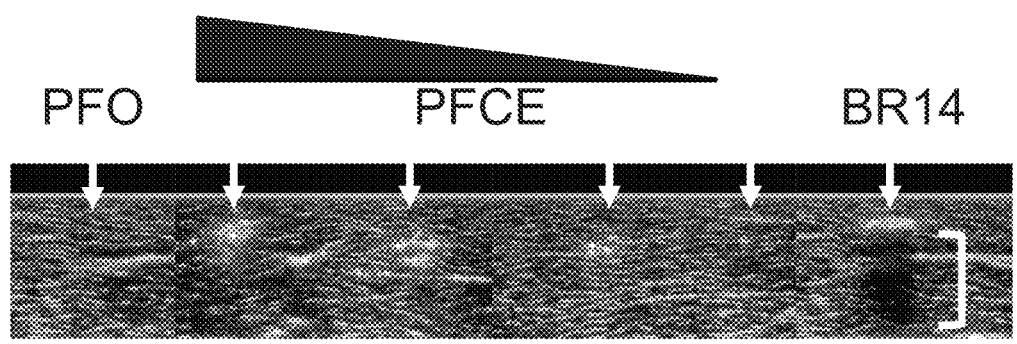
Figure 13D:
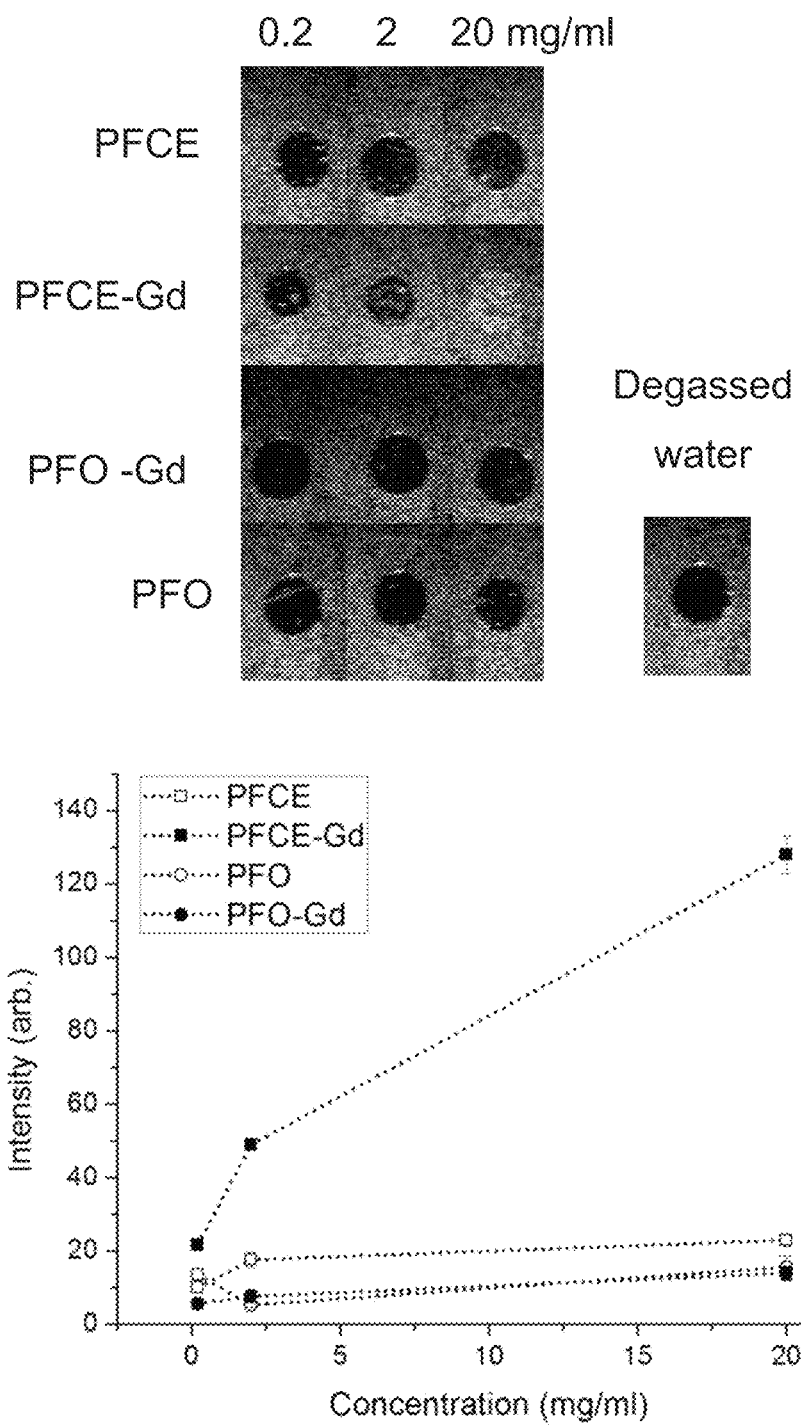
Figure 13E:
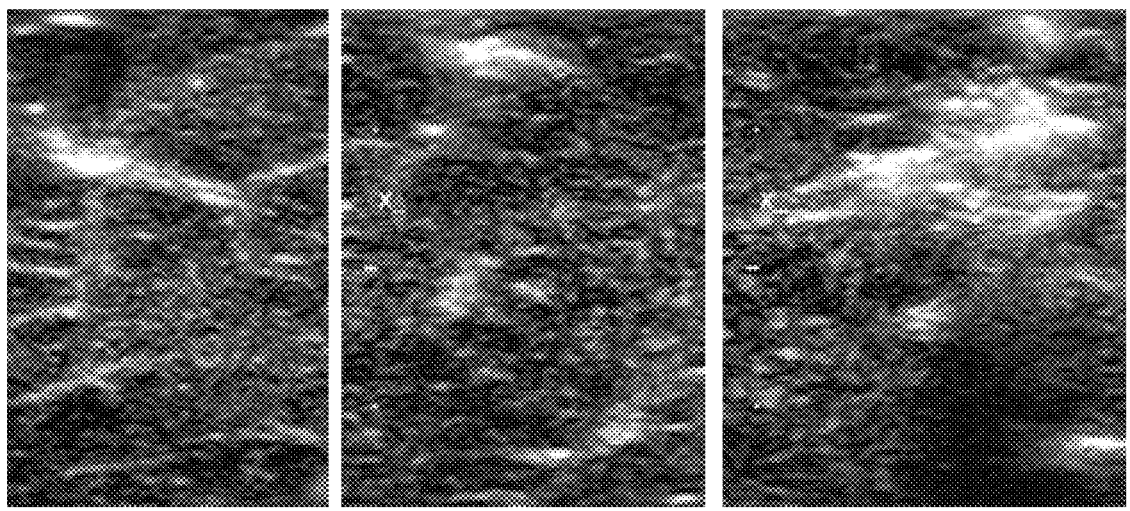
Figure 13F:

The particles consist of PLGA entrapping a PFC, with a diameter around 200 nm. Additional moieties such as fluorescent dyes or soluble metal chelates can be added. We focused on particles (FIG. 13A) containing perfluoro-15-crown-5-ether (PFCE) as the PFC, Gadoteridol (a soluble Gd chelate; Bracco Diagnostics Inc.) as this combination resulted in the best contrast for ultrasound and $^{19}$F MRI. The fluorescent dye IC-Green (Akorn Inc.) is also included, but not necessary for acoustic contrast. Similar PLGA particles with difference PFCs were tested in vitro in a gel phantom at various values of the mechanical index (MI) (FIG. 13B). We found that the PFCE particles with the Gd chelate (PFCE-Gd) showed the highest contrast at all MIs. We also found that the Gd content affects the ultrasound contrast (FIG. 13C), where concentrations of 40, 20, 10 and 0 µg of Gd per mg PFCE particles were tested; the highest Gd content results in the best contrast. The $^{19}$F content of the particles remained constant at 8×10$^{18}$ $^{19}$F's/mg. Here, BR14 microbubbles (Bracco) were used as a reference (perfluorobutane gas microbubbles with an average diameter of roughly 3000 nm). PFO particles were used as a negative control. Furthermore, the particles demonstrate a desirable high scattering to attenuation ratio (STAR) which is indicated by the smaller region of attenuation under the particles (highlighted under BR14 in the image). All further experiments were carried out with PFCE particles with the highest Gd content (PFCE-Gd$_{hi}$, unless indicated otherwise). In FIGS. 1d and e, particles were imaged either in gel phantoms or after injection in a tissue sample in vitro. FIG. 13D examines the relationship between particle concentration and contrast, with degassed water as a negative control. The signal intensities for regions of interest (ROIs) over the samples were plotted for comparison. A similar experiment was carried out using only the PFCE-Gd particles injected in tissue (FIG. 13E), where a clear relationship between concentration and signal also exists. Finally, we looked at energy-dispersive X-ray spectroscopy data (EDX) of the PFCE-Gd particles overlaid on corresponding electron microscopy (EM) images. The distributions for IC-Green, PFCE and Gd are shown. The Gd, and to a smaller extent IC-Green, appear to be distributed throughout the particle, while the PFCE seems more concentrated along the periphery, although still within the PLGA matrix. The distribution of Gd was different with similar particles made using a slightly different Gd chelate, gadobenate dimeglumine (MultiHance; Bracco), where the Gd was confined along the periphery of the particles as with the PFCE (data not shown). Interestingly, these particles did not show enhanced contrast in ultrasound images.

Particle Stability

Figure 14A:
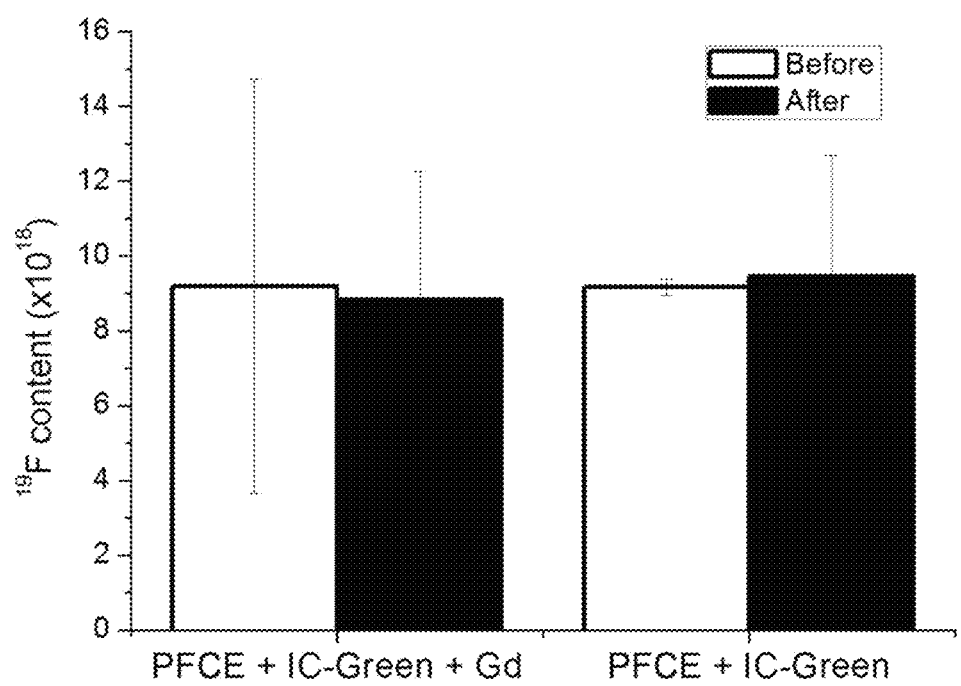
Figure 14B:
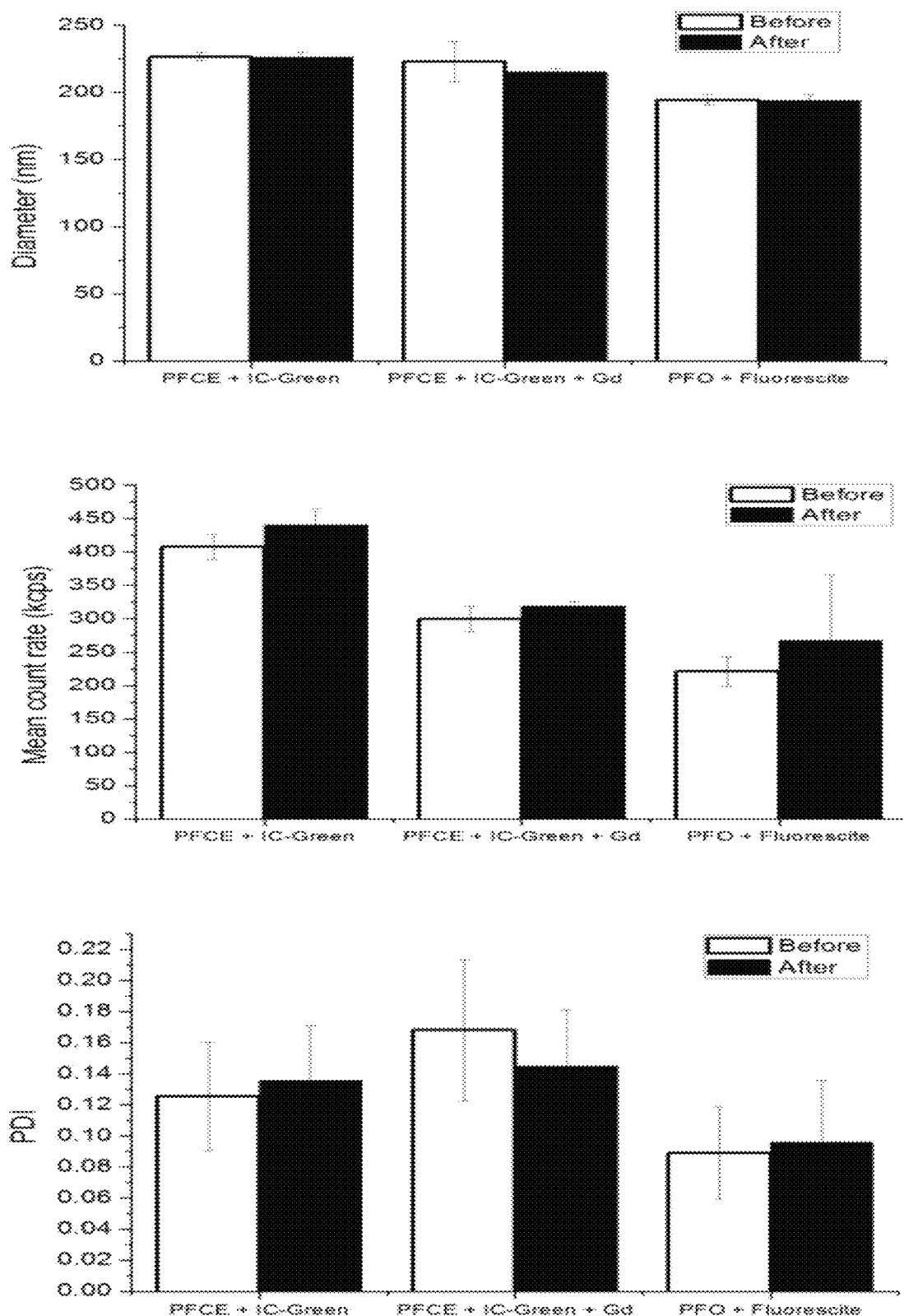
Figure 14C:
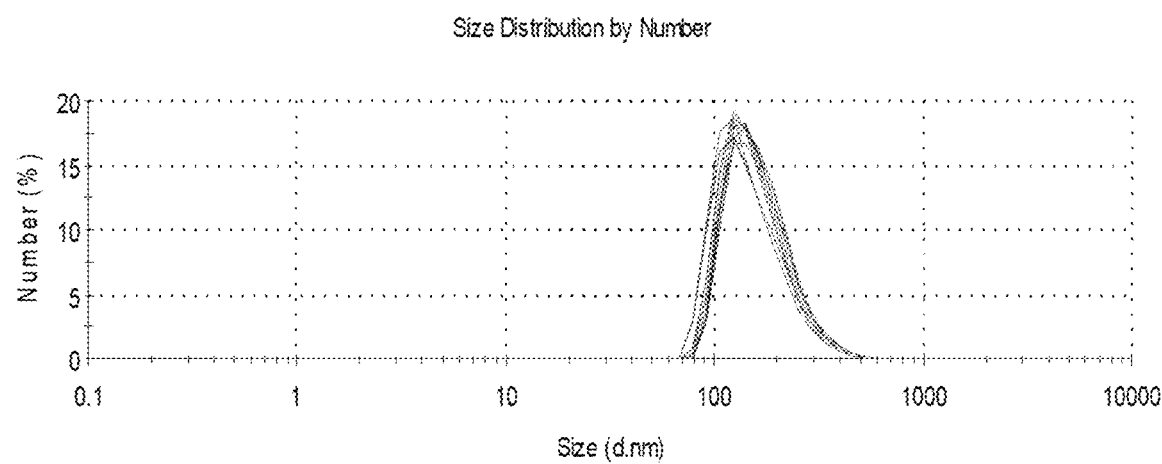

We show that the particles are stable to insonation, including extremely high energy probe sonication. PFCE-Gd particles were injected in vitro in a tissue sample, with tap water as a control (arrow, FIG. 6). The sample was imaged immediately, and 2 hours later, left at room temperature. No change in contrast from the particles was observed. All contrast due to the tap water (from dissolved air bubbles) dissipated immediately after injection, as the liquid spread through the tissue. We measured the fluorine content of particles containing PFCE, Gd and IC-Green or particles with PFCE and IC-Green only using $^{19}$F NMR, before and after exposure to ultrasound energy for 60 seconds (FIG. 14A). No change in PFCE content was apparent for either particle, indicating that the PFCE is not lost during the generation of acoustic contrast, as may be expected if the liquid PFCE vaporizes. Furthermore, no changes were observed in particle diameter, the mean count rate (indicative of the number of particles per unit volume) and the PDI (a measure of the spread of diameter distribution; FIG. 14B). These data show that the particles are not affected by the ultrasound energy. FIG. 14C shows representative droplet diameter distributions for the PFCE-Gd particles before and after insonation. No changes in droplet diameter distribution occur due to insonation. We observed the same when looking at particles using EM (FIG. 14E), although in these case we exposed the particles to probe sonication, which results in much higher energy deposition than ultrasound imaging. Finally, the particles can be readily stored for at least 6 months with no changes in DLS characteristics (not shown), as a lyophilised powder.

Acoustic Characterisation

The behaviour of the particles when irradiated by an ultrasound wave of increasing energy was measured (FIG. 15A), together with Sonovue microbubbles (Bracco; sulphur hexafluoride bubbles with average diameter of 2500 nm). The response for microbubbles rapidly collapses as the pressure increases due to loss of bubbles, while the particles show an increasing response. Pure liquid PFCE was used as a control. The other particles tested are PFCE and PFCE with high and low Gd content (PFCE-$Gd_{hi}$ and PFCE-$Gd_{lo}$).

The acoustic activity and echogenicity of the particles was quantified using a method based on acoustic radiation force[16]. The signal backscattered by an ultrasound contrast agent and the radiation force acting on it have the same origin and therefore a measure of the scattering coefficient can be achieved by measuring the displacement in a defined acoustic field (FIG. 15B). A piezo element was used to generate a standing wave in a square glass capillary, with homogeneously dispersed particles. The creation of an ultrasound standing wave induces migration towards the pressure node or antinode located in the middle and the sides of the channel respectively within a few seconds. The motion of the particles was recorded with a high-speed camera and analysed (FIG. 15C).

The forces acting on a random particle in an acoustic field include the drag force[17], the added mass force that describes the acceleration of the surrounding fluid subsequent to the motion[18] of the particle and the radiation force that drives the motion of the particle. The momentum conservation equation can be written from these three forces in order to determine the trajectory of a particle of given size. In a first approximation, the particles are assumed to obey the well-accepted theory describing the interaction of a rigid sphere with a random acoustic field[16]. The radiation force can be decomposed in two participations coming from the field decomposition on the spherical harmonics where $f_1$ is only dependant on the relative density and $f_2$ only on the relative compressibility. The radiation force ($F_r$) on a particle in a standing wave is then:

$$F_r = \frac{V_p P_a^2}{4\rho_0 c_0^2}\left[f_1 + \frac{3}{2}R_{eal}(f_2)\right]\sin(2ky)$$

where $\rho_0$ is the mass density of the fluid, $P_a$ is the pressure of the acoustic wave, $V_p$ the volume of the particle, $c_0$ the speed of sound in the fluid and k the wave vector.

It can be shown that for a polymer nanoparticle the imaginary part of the coefficient $f_2$ can be neglected. The backscattered pressure then relates to the radiation force in the direction of the transducer by:

$$p_{sc} = \frac{P_a}{r}\frac{k\rho_0 c_0^2}{\pi}\frac{Fr\left(y=\frac{\lambda}{8}\right)}{P_a^2}$$

From this expression, the scattering cross section in intensity can be defined as the total scattered power over the incoming intensity:

$$\sigma_{sc} = \left(\frac{rp_{sc}}{P_a}\right)^2 = \left(\frac{k\rho_0 c_0^2}{\pi}\frac{Fr\left(y=\frac{\lambda}{8}\right)}{P_a^2}\right)^2$$

Ultrasound contrast originates from the pressure wave reflected by non-flat interfaces or scattered from small scatterers either present in the tissues or artificially injected. Scattering from particles can occur through geometrical scattering, which is the case for most particles and corresponds to the theory presented in the equations, or resonant vibrational behaviours for contrast bubbles for example that scatter an acoustic wave by high amplitude radial vibrations. The scattering cross section then represents the efficient section over which the acoustic intensity is absorbed by the particle to be reemitted in a spherical manner and is quadratically related to the contrast generation. The efficient cross-section for the samples is presented in FIG. 15D. The dashed blue line depicts the scattering behaviour of a coated bubble typically used for ultrasound contrast generation accordingly to the Rayleigh-Plesset theory[19]. The geometric scattering for these contrast bubbles is lower than the vibrational scattering in the range considered and is therefore neglected. PFCE-Gd particles, not PLGA or PFCE only, show a scattering coefficient 8 orders of magnitude higher than predicted for a bubble of the same size (FIG. 15D). Interestingly, the scattering coefficient of most particles was similar to that expected for a coated bubble of comparable size. However, such small bubbles are highly unstable and cannot be used in practice. Furthermore the preparation of the particles with PFCE dramatically modifies their behaviour and improves their efficiency, particularly upon addition of Gd. Contrary to the other samples, the PFCE-based nanoparticles moved toward the pressure antinode (FIG. 15C) as would a small bubble and present a scattering coefficient increased by 2 orders of magnitude compared to bubbles of the same size (FIG. 15D). Ultra high speed imaging of the particles[20] showed no change to the particles with insonation (data not shown).

Cell Labelling and Imaging

Figure 16B:
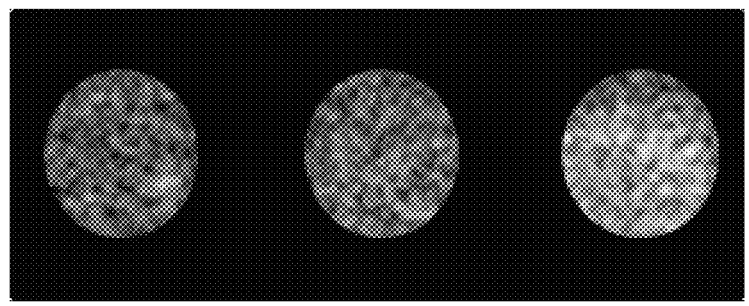
Figure 16C:
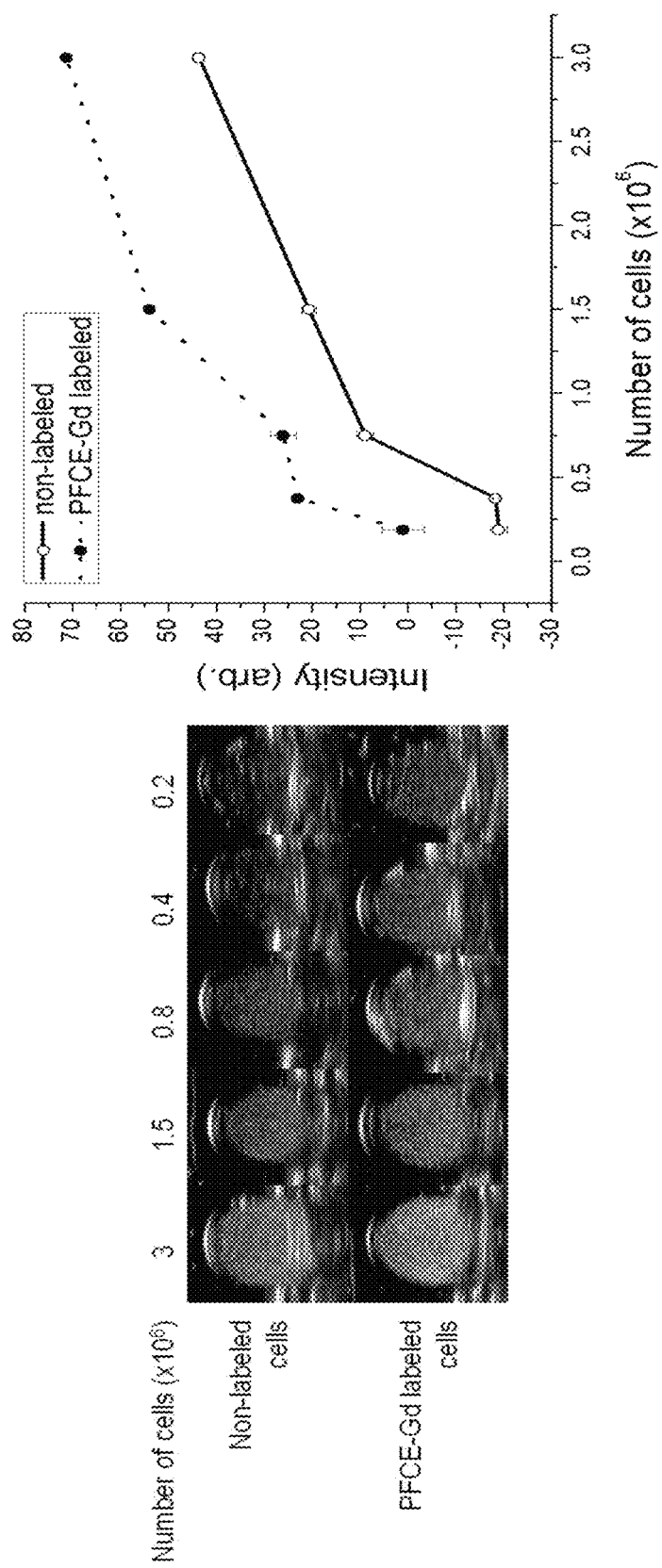

Primary human DCs as used in clinical trials[2] were labeled and imaged. No effect on cell viability was observed relative to non-labeled controls. Previous work with similar particles, except without the Gd chelate, has shown no effect of labeling on cells with respect to the expression of maturation markers, ability to activate T cells and migratory ability[21, 22]. Labeled cells were readily detected using fluorescence, MR and ultrasound imaging after injection in a tissue sample ex vivo (FIG. 16A). 2 million labeled cells were injected. Ultrasound imaging was carried out first, followed by fluorescence and MR imaging; the persistence of fluorescence and particularly $^{19}$F MRI signal indicates that the particles are not damaged by exposure to ultrasound. FIG. 16B shows 10 million DCs in a gel phantom, where the cells were either non-labeled, labeled with PFO particles or with PFCE-Gd particles. Again, it is clear that the cells labeled with PFCE-Gd particles show the highest contrast. Finally, a dilution series of these cells was made and imaged using ultrasound (FIG. 16C). 3-0.2 million labeled or non-labeled cells were imaged. The relative intensity for an ROI encompassing the wells is plotted, showing that a clear enhancement of contrast.

In Vivo Imaging and Toxicity

Figure 17A:

PFCE-Gd particles were injected intramuscularly in a mouse (FIG. 17A). Images are shown before, immediately after and 2 hours after injection. The mouse was anesthetised during injection, but was then allowed to recover before the next imaging session. Thus, the particles dispersed within the muscle to some extent due to the movement of the mouse. Furthermore, it is not possible to obtain exactly the same imaging plane as with the previous images. Despite these issues, the injected particles are still clearly detectable. These images were acquired on a clinical ultrasound scanner.

Figure 17B:
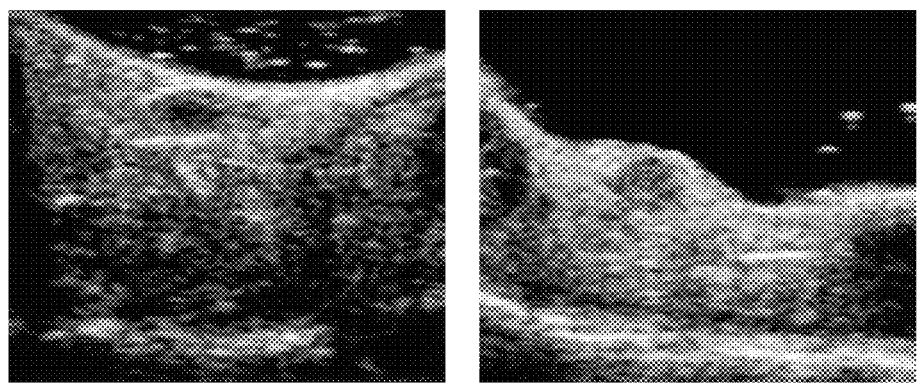
Figure 17C:
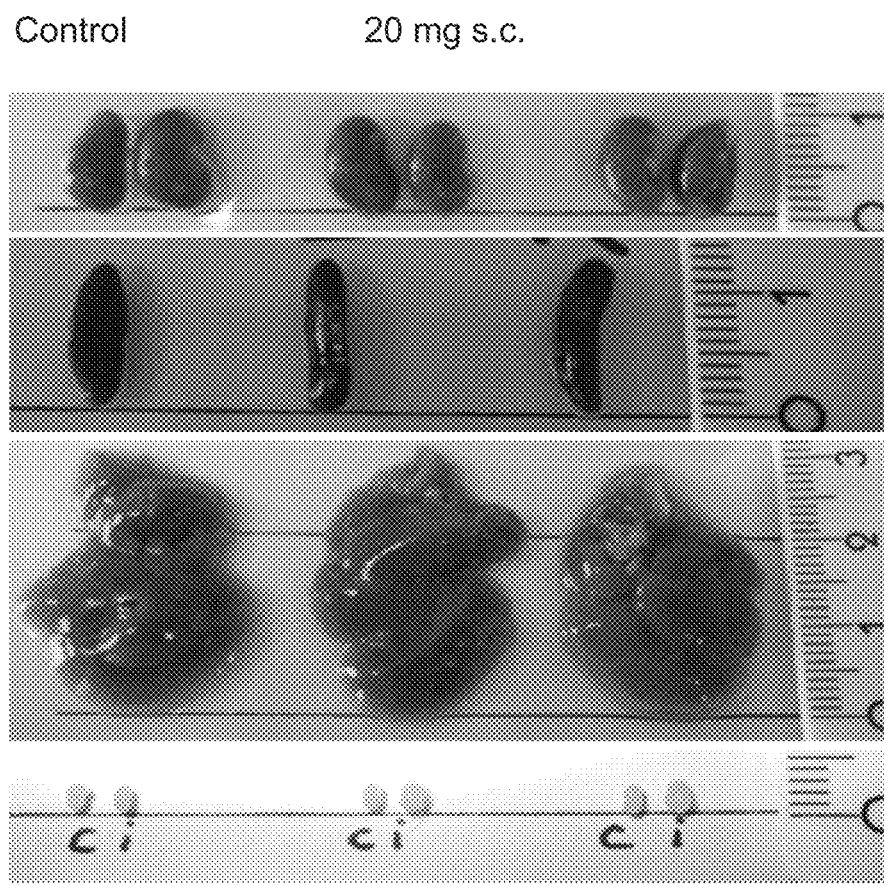

Particles were imaged after intranodal injections in mice (FIG. 17B). These injections mimic the clinical situation, where cells can be injected directly in the lymph nodes of patients in DC vaccination therapy[23]. However, due to the small volume that can be injected in murine lymph nodes (less than 10 µl), only particles (0.1 mg) were injected in place of cells. In these experiments, 0.1 mg corresponds to 100,000 cells, given a constant cell uptake, while typically 3-15 million cells are injected in clinical trials. High resolution ultrasound was carried out at 21 MHz, in order to localize the lymph nodes which typically under 2 mm in their long axis. The mean contrast of the node changed over 10-fold after injection of the particles. No contrast was detected at 18 hours post-injection (not shown). Fluorescence signal was also not detected, even with excised lymph nodes, further suggesting that the particles were cleared from the injected node.

Finally, we studied the toxicity of the particles (FIG. 17C) in mice injected subcutaneously with 20 mg of the particles, which is a very large dose. The mice were monitored for 2 weeks, relative to noninjected controls. No changes in weight, behaviour or appearance was observed during this period. At the end-point, mice were sacrificed and their organs weighed and examined. No significant differences were observed relative to control animals; in particular, the kidneys, spleens, livers and draining lymph nodes were closely examined. Taken together with the lack of effect after cell labeling and evidence for clearance, these data indicate that the particles are biocompatible.

Example 16

Further Procedures and Methods

Particle Synthesis

Particles were made as described previously[22], with the addition of gadoteridol from ProHance (Bracco Imaging Europe, Amsterdam). Briefly, 1 g polyvinyl alcohol dissolved in 50 ml water only or water and ProHance, 1780 µl for $Gd_{hi}$ and 1400 for $Gd_{lo}$, is added dropwise to 180 mg of PLGA (Resomer RG 502 H, lactide: glycolide molar ratio 48:52 to 52:48; Boehringer Ingelheim, Germany) dissolved in dichloromethane with 890 µl PFCE (Exfluor Inc, Texas USA) or 232 µl PFO (Perfluoron, Alcon Inc), on ice, with sonication using a Digital Sonifier 250 (Branson, Danbury, USA) with a cuphorn running at 40% power for 2 minutes in 10 second pulses. Dynamic light scattering was done on a Malvern Zetasizer Nano. Gd content was measured using mass spectrometry. PFCE-$Gd_{lo}$ particles contain 20 µg/mg and PFCE-$Gd_{hi}$ 40 µg/mg.

In Vitro Imaging

In vitro ultrasound imaging was carried out on samples in a gel phantom or injected in bovine liver tissue using a Philips SONOS 7500 scanner using a linear array transducer (11-3L) with a centre frequency of 7.5 MHz. MI values were limited to 0.2. A linear array transducer (L11-3) with central frequency 7.5 MHz was used for all the ultrasound scans (SONOS 7500, Philips Medical Systems, Best, The Netherlands). The MI was variable, from 0.1-2.0, as stated in the text. Gain was typically set to 90%.

Gel phantoms consisted of 8% gelatin (Dr. Oetker, Ede, The Netherlands) and 2% agar (Agar Powder CMN, Boom, Meppel, The Netherlands) by weight solution (these gels showed as bright in the ultrasound images), or PolyVinyl Alcohol Cryogel (15% by weight PVA (Boom, Meppel, The Netherlands), 20% by weight cooling liquid (Koelvloeistof Basic Safe, Halfords, The Netherlands), and 65% by weight water was heated to ~90 degrees Celsius in a closed cylinder until a homogeneous liquid was formed. After pouring in a mold and one freeze-thaw cycle (12 hours at −25° C. and subsequently 12 hours at 20° C.)).). Analyses on the contrast (FIG. 13D) was carried out by drawing a region of interest over the wells and measuring average pixel intensity using Image J (U. S. National Institutes of Health, Bethesda, Md., USA).

MR imaging and spectroscopy was performed on a 11.7T MR system (Bruker Biospin, Ettlingen, Germany), equipped with a horizontal bore magnet, using a dual $^1H/^{19}F$ volume coil. Image settings were TR/TE of 800/10.5 ms, 2×2×2 mm voxels, 256×128 matrix and 2 averages for $^1H$ using a spin echo sequence; 960/46 ms, 4×4×4 mm voxels, 64×32 matrix, 512 averages using a RARE sequence with RARE factor 8.

For fluorescence imaging, mice or sample tubes were placed in a FluorVivo 300 (INDEC BioSystems, Santa Clara, Calif. USA). Exposure times were between 0.05 and 0.15 s.

Cell Isolation and Labelling

Primary human DCs were isolated from donor blood as described[21], and labelled with 5 mg of particles per million cells from days 3-8 of the in vitro culture period. Cells were washed extensively (three times) before use. Viable cells were counted using a cell counter with trypan blue exclusion.

In Vivo Imaging

Mice were housed under specified pathogen-free conditions in the Central Animal Laboratory (Nijmegen, the Netherlands). All experiments were performed according to the guidelines for animal care of the Nijmegen Animal Experiments Committee. In vivo ultrasound imaging was carried out using a VisualSonics Vevo 2100 system with a MS550S transducer. Mice were anasthesised using Isoflurane.

Intranodal injections were performed with a NanoFil Microliter syringe (World Precision Instruments, Germany) under microscopic guidance.

EM and EDX Measurements

The sample was fixed on a glass plate by evaporation of the suspension fluid. A layer of gold was then deposited on the sample before observation by an environmental scanning electron microscope FEI ESEM XL30 at 20 kV and magnifications up to 60.000×.

Transmission electron microscopy (TEM) and TEM-EDS, TEM coupled with energy dispersive X-ray spectroscopy (EDS) was performed on a state of the art 200 KV JEOL TEM 2100 system with a resolution point of 0.24 nm. The microscope is equipped with two Gatan camera's: Gatan 833 Onus and Gatan 890 ultrascan for the highest resolution and sensitivity at an acceleration voltage of 200 kV and two detector systems STEM and EDS (energy dispersive X-ray spectroscopy for elemental analysis. Standard specimen holder for TEM measurements and a Beryllium specimen holder, for EDS measurements were used. Sample specimens were prepared by placing a drop (6-10 ul) of the solution on a carbon-coated Cu grid (200 mesh, EM science) and air-dried. The TEM images allowed for visualization of the nanoparticles and their size distribution while the secondary electron imaging allowed for the examination of the chemical composition of the nanoparticles and the elemental mapping and elemental imaging distribution.

Acoustic Characterisation

Figure 15A:
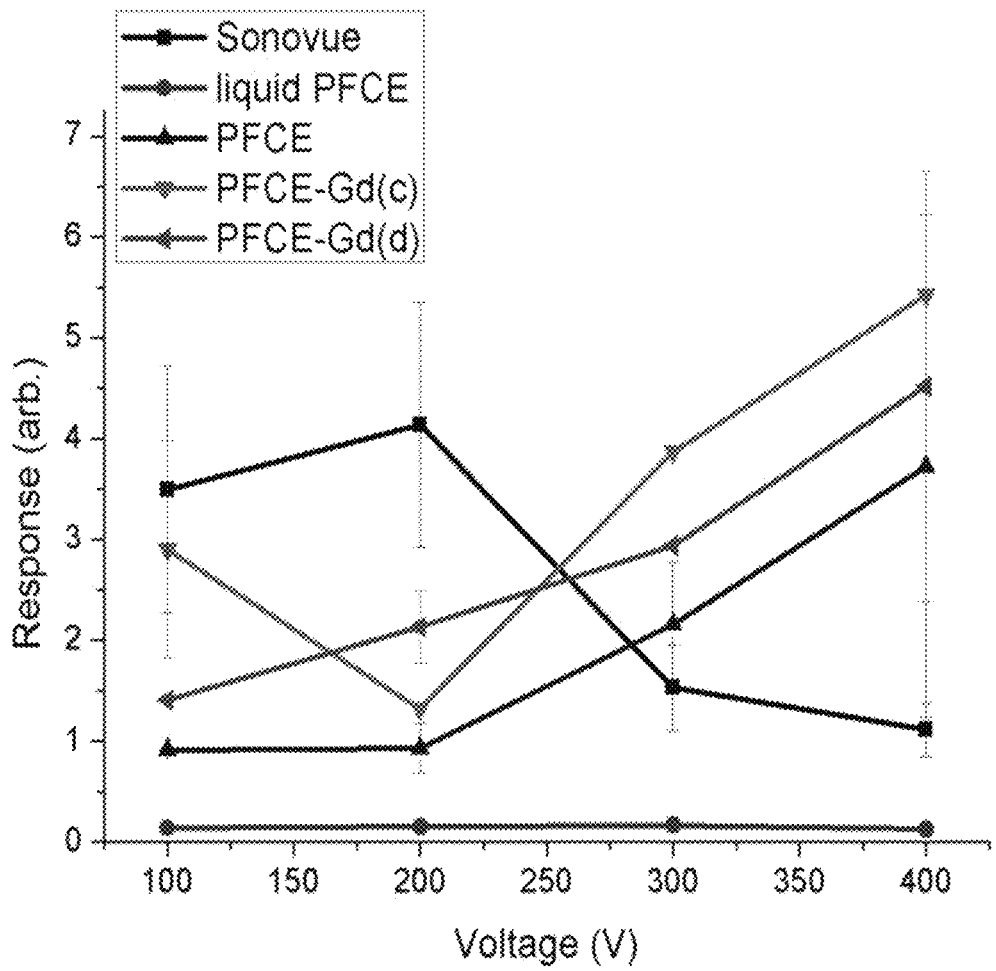
Figure 15B:
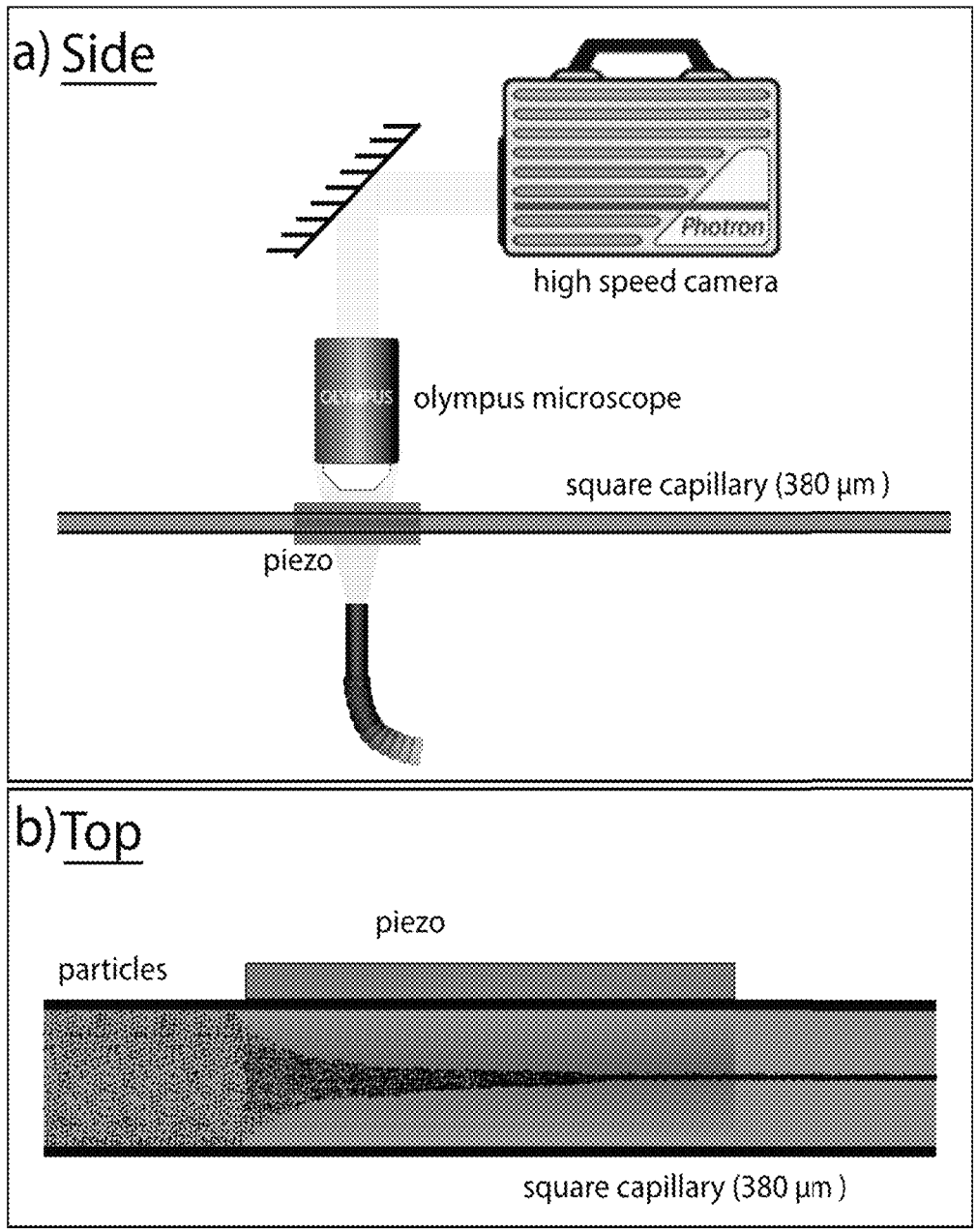
Figure 15C:
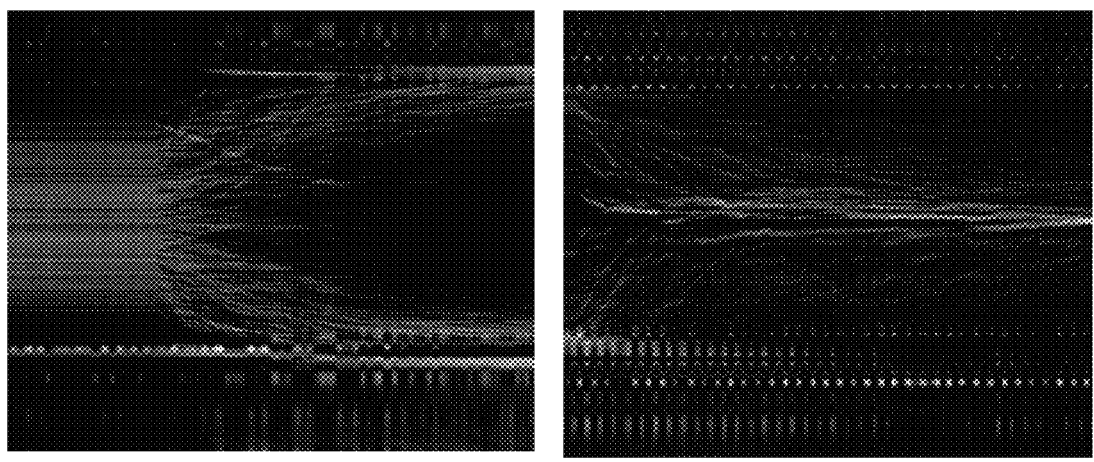
Figure 15D:
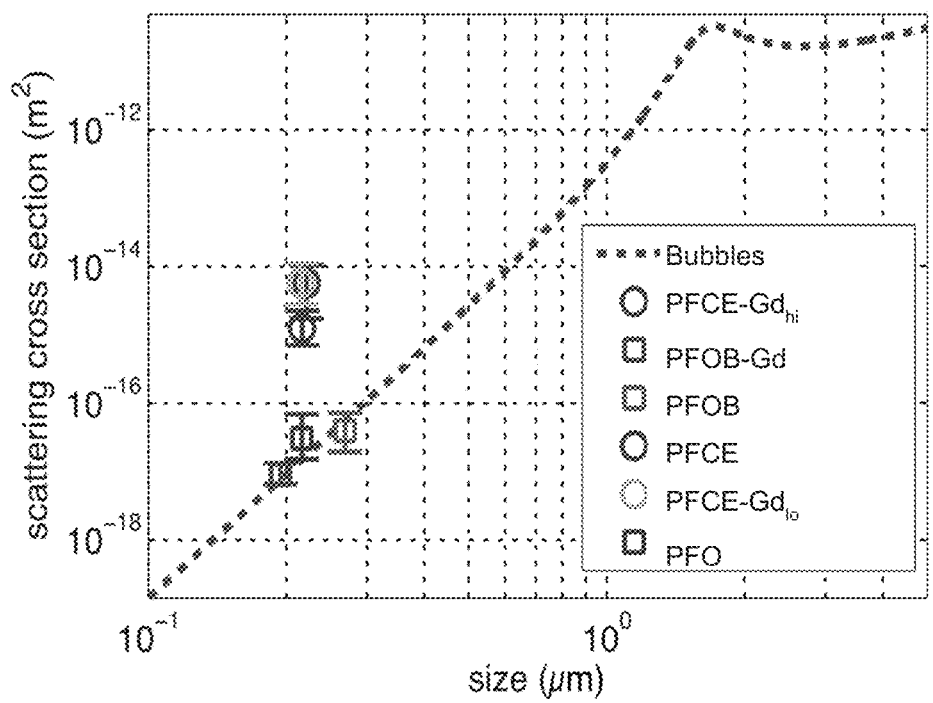

The results presented in FIG. 15A were obtained using a Panametrics 5077PR pulser receiver connected to a Panametrics 5 MHz A308S tranducer. A sample holder containing 4 4 mm thick cuvettes was made out of polydimethylsiloxane (PDMS) and placed at the focus of the transducer. A water reference was taken for each series. The experimental setup consisted in a squared capillary of about 380 micrometers in size attached to a piezoelectric crystal in order to generate an acoustic standing wave in the capillary at the frequency of 1.94 MHz as depicted in FIG. 15B. The motion of the particles is recorded at 125 frames per second by the use of a photron APX high-speed camera connected to an Olympus microscope. A 10× objective is used for the visualization. The signals were generated with a Tabor AWG arbitrary waveform generator and amplified with an ENI 350 L power amplifier. Due to the rapid building up of streaming, the experiments were realized at low pressures to limit the impact of the streaming in the fluid. The analysis is achieved using Matlab®. In particular the PIV curves are obtained using OpenPIV, freely available software. Two methods were used simultaneously to analyse the optical recording for more precision. The first is a PIV analysis, which is based on the cross correlation of the sub matrices of the image. A relative displacement can be obtained from the PIV analysis and rescaled to the known geometry. A second method is based averaging in the horizontal direction. The resulting pixel line is added to the previous ones in a single frame as presented in FIG. 15C.

In Vivo Toxicity Test 20 mg of particles were injected s.c. in mice, and the mice observed for 2 weeks relative to untreated controls. The organs were removed for observation and weighing after the 2 week period.

Example 17

Further Discussion

PFCs have unique acoustic properties, especially with regards to a very low speed of sound[24] which may influence their contrast properties. PFC droplets have previously been used for ultrasound, although these require vaporisation of the PFC, and tend to be submicron-sized[7, 15, 25-28]. PFCs have also been mixed with metals for use as contrast agents, typically for MRI. However, these tend to be with solid metal nanoparticles, such as iron oxide crystals[29 30]. The role of a soluble Gd chelate, and specifically gadoteridol as opposed to other similar chelates, is evident in our data (e.g. FIG. 13C), but remains undefined. There is no literature on the enhancement of acoustic signal using soluble metal chelates, although solid metal particles are frequently used as ultrasound CAs[29, 31-33]. Thus, there is currently no literature on soluble metal chelates enhancing liquid PFCs, which remain in liquid form, for ultrasound. Evidence that the PFCE remains liquid in our particles include its high boiling point (145° C.), the lack of changes in DLS and EM data, and fluorine content (FIG. 14), and the ability to perform $^{19}$F MRI even after insonation (FIG. 16A).

The acoustic activity of the particles was undeniably observed and measured in the experiments presented even if the precise mechanism by which the particles backscatter the ultrasound waves remains vague. Ultra high-speed recordings[20] rule out any cavitation events. In addition, the low pressures used for the acoustics characterization (15 kPa) leave little possibility for non-linear effects or cavitation. Therefore new mechanisms have to be investigated. This work cannot be realized with a typical 90° setup as theories predicts directivities of the scattered waves, which also seems indicated by the low shadow of the particles (FIG. 13C). More complex theories[34 35] will need to be investigated in order to account for potential effects of the shell on the acoustic behaviour. An exhaustive acoustic study to fully unravel the physical mechanism is beyond the scope of the current work. For now, we suspect a non-trivial form of resonance of the particles to explain the strength of the received signal as all mechanical resonances for this kind of system are given at much higher frequencies.

The PLGA particles containing PFCs have previously shown excellent cell uptake with minimal toxicity. In fact the cellular $^{19}$F loading, a key parameter for $^{19}$F MRI studies, achieved with these particles is the highest reported so far[36]. The addition of the Gd chelate is not expected to significantly affect the uptake or other characteristics of the particles, due to its extremely low concentration. Moreover, the Gd content is several orders of magnitude lower than the current recommended clinical dose (Table 1). The same is true for the PLGA, PFC and IC-Green (Table 1). The clearance of these components has also been well-studied. This is an important advantage over other stable ultrasound contrast agents, which are typically solids such as gold or silica nanoparticles[9 10 11], and tend to have long in vivo retention times[12] and less clinical applicability[13].

Figure 14D:
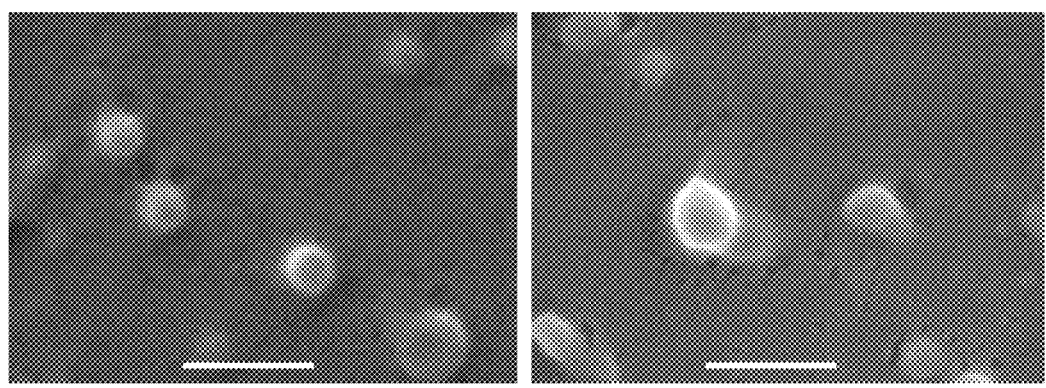

The 200 nm PLGA particles with PFCE and Gd chelate (Gadoteridol, Bracco) described here produce high acoustic contrast, without being affected by the ultrasound energy. In particular, the particles are small enough to leave the circulation—a major limitation of current microubble agents, which are restricted to the circulation due to their larger size and shorter lifetime. Furthermore, the particles are also stable to high energy probe sonication (FIG. 14D). Such stability is essential for long-term applications such as in vivo targeting to regions outside the endothelium, and to cell labeling. We have also shown that the particles can be used for contrast generation at high frequencies (FIG. 17B), which allows high resolution imaging and thus the development of small animal models for ultrasound-based imaging studies. The particles can readily be made for clinical use under GMP conditions. This together with the lack of toxicity observed both to cells and in vivo, demonstrates their suitability for human use. PLGA particles have also been extensively applied in the literature to various uses such as targeted drug and vaccine delivery, and subjected to various modifications including the addition of radioligands[37] and coating with PEG to make "stealth" particles[38]. The rate of particle degradation and subsequent drug release rate, circulation times and multimodal functionalities can be controlled[39 22 40]. All of these modifications remain possible with our particles, allowing further customization where necessary.

Ultrasound imaging is ideally suited to the study of personalised therapeutics, but its potential is unrealized due to the lack of suitably stable, biocompatible contrast agents. The particles described here can be readily customised to multimodal imaging in clinical and preclinical applications, including cell tracking and targeted drug delivery.

TABLE 1

| Compound | Prior human use | Recommended dose | Estimated dose (per million DCs) | Clearance route |
|---|---|---|---|---|
| PLGA | Scaffolds, particles for vaccine delivery[41] | Varies with application; typically 30 mg | <1 mg | normal cell metabolism |
| PFC e.g. Perfluoron (Alcon Inc) Oxygent (Alliance Pharma) PFCE | eye surgery blood substitute $^{19}$F MRI signal[42] | 8 mg >100 g n/a | 0.1-0.3 ng (dependant on DC subset) | exhalation in lungs; PFCs are not metabolized in vivo |
| Gd chelate e.g. ProHance Multihance (both Bracco) | intraveneous contrast agent for $^1$H MRI | 4000 mg | <1 mg | removed by the kidneys |
| IC-Green (Pulsion) | intraveneous contrast | 35 mg | <5 mg | removed by the kidneys |

REFERENCES

1. Srinivas, M. et al. Imaging of cellular therapies. *Adv Drug Deliv Rev* 62, 1080-1093 (2010).
2. Aarntzen, E. H. et al. Early identification of antigen-specific immune responses in vivo by [18F]-labeled 3'-fluoro-3'-deoxy-thymidine ([18F]FLT) PET imaging. *Proc Natl Acad Sci USA* 108, 18396-18399 (2011).
3. Aarntzen, E. H. et al. Targeting of 111In-labeled dendritic cell human vaccines improved by reducing number of cells. *Clin Cancer Res* 19, 1525-1533 (2013).
4. Qin, S., Caskey, C. F. & Ferrara, K. W. Ultrasound contrast microbubbles in imaging and therapy: physical principles and engineering. *Phys Med Biol* 54, R27-57 (2009).
5. Sirsi, S. & Borden, M. Microbubble Compositions, Properties and Biomedical Applications. *Bubble Sci Eng Technol* 1, 3-17 (2009).
6. Kiessling, F., Huppert, J. & Palmowski, M. Functional and molecular ultrasound imaging: concepts and contrast agents. *Curr Med Chem* 16, 627-642 (2009).
7. Reznik, N. et al. The efficiency and stability of bubble formation by acoustic vaporization of submicron perfluorocarbon droplets. *Ultrasonics* 53, 1368-1376 (2013).
8. Aggeli, C., Giannopoulos, G., Lampropoulos, K., Pitsavos, C. & Stefanadis, C. Adverse bioeffects of ultrasound contrast agents used in echocardiography: true safety issue or "much ado about nothing"? *Curr Vasc Pharmacol* 7, 338-346 (2009).
9. Delogu, L. G. et al. Functionalized multiwalled carbon nanotubes as ultrasound contrast agents. *Proc Natl Acad Sci USA* 109, 16612-16617 (2012).
10. Jokerst, J. V., Khademi, C. & Gambhir, S. S. Intracellular aggregation of multimodal silica nanoparticles for ultrasound-guided stem cell implantation. *Sci Transl Med* 5, 177ra135 (2013).
11. Chung, E., Nam, S. Y., Ricles, L. M., Emelianov, S. Y. & Suggs, L. J. Evaluation of gold nanotracers to track adipose-derived stem cells in a PEGylated fibrin gel for dermal tissue engineering applications. *Int J Nanomedicine* 8, 325-336 (2013).
12. Longmire, M., Choyke, P. L. & Kobayashi, H. Clearance properties of nano-sized particles and molecules as imaging agents: considerations and caveats. *Nanomedicine (Lond)* 3, 703-717 (2008).
13. Lin, C., Fugetsu, B., Su, Y. & Watari, F. Studies on toxicity of multi-walled carbon nanotubes on Arabidopsis T87 suspension cells. *J Hazard Mater* 170, 578-583 (2009).
14. Kang, S. T. & Yeh, C. K. Intracellular acoustic droplet vaporization in a single peritoneal macrophage for drug delivery applications. *Langmuir* 27, 13183-13188 (2011).
15. Strohm, E. M., Min Rui, Michael C Kolios, Ivan Gorelikov, Naomi Matsuura in IEEE International Ultrasonics Symposium Proceedings 495-4982010).
16. Settnes, M. & Bruus, H. Forces acting on a small particle in an acoustical field in a viscous fluid. *Phys Rev E Stat Nonlin Soft Matter Phys* 85, 016327 (2012).
17. Mettin, R. & Doinikov, A. A. Translational instability of a spherical bubble in a standing ultrasound wave. *Applied Acoustics* 70, 1330-1339 (2009).
18. Magnaudet, J. & Eames, I. The Motion of High-Reynolds-Number Bubbles in Inhomogeneous Flows. *Annual Review of Fluid Mechanics* 32, 659-708 (2000).
19. Leighton, T. G. The Acoustic Bubble. (Academic Press, 1996).
20. Gelderblom, E. C. et al. Brandaris 128 ultra-high-speed imaging facility: 10 years of operation, updates, and enhanced features. *Rev Sci Instrum* 83, 103706 (2012).
21. Bonetto, F. et al. A large-scale (19)F MRI-based cell migration assay to optimize cell therapy. *NMR Biomed* 25, 1095-1103 (2012).
22. Srinivas, M. et al. Customizable, multi-functional fluorocarbon nanoparticles for quantitative in vivo imaging using 19F MRI and optical imaging. *Biomaterials* 31, 7070-7077 (2010).
23. Aarntzen, E. H. et al. In vivo imaging of therapy-induced anti-cancer immune responses in humans. *Cell Mol Life Sci* 70, 2237-2257 (2013).
24. Strohm, E. M., Michael C. Kolios in IEEE International Ultrasonics Symposium 2368-23712011).
25. Matsunaga, T. O. et al. Phase-change nanoparticles using highly volatile perfluorocarbons: toward a platform for extravascular ultrasound imaging. *Theranostics* 2, 1185-1198 (2012).
26. Reznik, N. et al. Optical studies of vaporization and stability of fluorescently labelled perfluorocarbon droplets. *Phys Med Biol* 57, 7205-7217 (2012).
27. Sheeran, P. S., Luois, S. H., Mullin, L. B., Matsunaga, T. O. & Dayton, P. A. Design of ultrasonically-activatable nanoparticles using low boiling point perfluorocarbons. *Biomaterials* 33, 3262-3269 (2012).
28. Szijjarto, C., Rossi, S., Waton, G. & Krafft, M. P. Effects of perfluorocarbon gases on the size and stability characteristics of phospholipid-coated microbubbles: osmotic effect versus interfacial film stabilization. *Langmuir* 28, 1182-1189 (2012).
29. Li, A. et al. Superparamagnetic perfluorooctylbromide nanoparticles as a multimodal contrast agent for US, MR, and CT imaging. *Acta Radiol* 54, 278-283 (2013).
30. Barnett, B. P. et al. Use of perfluorocarbon nanoparticles for non-invasive multimodal cell tracking of human pancreatic islets. *Contrast Media Mol Imaging* 6, 251-259 (2011).
31. Li, F. et al. Preparation of gold nanoparticles/functionalized multiwalled carbon nanotube nanocomposites and its glucose biosensing application. *Biosens Bioelectron* 24, 1765-1770 (2009).
32. Niu, C. et al. Doxorubicin loaded superparamagnetic PLGA-iron oxide multifunctional microbubbles for dual-mode US/MR imaging and therapy of metastasis in lymph nodes. *Biomaterials* 34, 2307-2317 (2013).
33. Niu, D. et al. Facile synthesis of magnetite/perfluorocarbon co-loaded organic/inorganic hybrid vesicles for dual-modality ultrasound/magnetic resonance imaging and imaging-guided high-intensity focused ultrasound ablation. *Adv Mater* 25, 2686-2692 (2013).
34. Strifors, H. C. & Gaunard, G. C. Differences in the acoustic echoes from submerged elastic shells containing different fluids. *Ultrasonics* 30, 107-112 (1992).
35. Kovalev, V. A. Matching of asymptotic approximations in the problem of the scattering of acoustic waves by an elastic spherical shell. *Journal of Applied Mathematics and Mechanics* 66, 581-590 (2002).
36. Srinivas, M., Boehm-Sturm, P., Figdor, C. G., de Vries, I. J. & Hoehn, M. Labeling cells for in vivo tracking using (19)F MRI. *Biomaterials* 33, 8830-8840 (2012).
37. D'Souza, M. & DeSouza, P. Preparation and testing of cyclosporine microsphere and solution formulations in the treatment of polyarthritis in rats. *Drug Dev Ind Pharm* 24, 841-852 (1998).
38. Avgoustakis, K. Pegylated poly(lactide) and poly(lactide-co-glycolide) nanoparticles: preparation, properties and possible applications in drug delivery. *Curr Drug Deliv* 1, 321-333 (2004).
39. Mahapatro, A. & Singh, D. K. Biodegradable nanoparticles are excellent vehicle for site directed in-vivo delivery of drugs and vaccines. *J Nanobiotechnology* 9, 55 (2011).
40. Jain, A. K., Das, M., Swarnakar, N. K. & Jain, S. Engineered PLGA nanoparticles: an emerging delivery tool in cancer therapeutics. *Crit Rev Ther Drug Carrier Syst* 28, 1-45 (2011).
41. Lu, J. M. et al. Current advances in research and clinical applications of PLGA-based nanotechnology. *Expert Rev Mol Diagn* 9, 325-341 (2009).
42. Hahn, T. et al. Visualization and quantification of intestinal transit and motor function by real-time tracking of 19F labeled capsules in humans. *Magn Reson Med* 66, 812-820 (2011).

What is claimed is:

1. A method of ultrasound imaging a subject, wherein the imaging consists of amplitude-based ultrasound imaging, the method comprising:
providing to the subject a poly(lactic-co-glycolic) acid (PLGA) particle comprising a liquid perfluoro crown ether selected from the group consisting of perfluoro-15-crown-5-ether, perfluoro-12-crown-4-ether, and perfluoro-18-crown-6-ether; and gadoteridol, wherein the PLGA of the particle is present in the form of a matrix, wherein the gadoteridol and liquid perfluoro crown ether are distributed in the matrix, and
imaging the particle using the amplitude-based ultrasound, wherein the particle provides enhanced contrast during imaging as compared to imaging performed without the particle comprising the gadoteridol, wherein the liquid perfluoro crown ether remains in liquid form during the imaging, wherein the particle is essentially surfactant free or surfactant free.

2. The method according to claim 1, wherein the particle is comprised in a particulate matter wherein the mean particle diameter is of a value of between 100 and 300 nanometers.

3. The method according to claim 1, wherein the mean particle diameter is of a value of between 150 and 250 nanometers.

4. The method according to claim 1, wherein the mean particle diameter is 200 nanometers.

5. The method according to claim 1, wherein the particle comprises a detecting agent, such as a dye, such as a fluorescent dye or a radionuclide.

6. The method according to claim 1, wherein the particle comprises a therapeutic agent, such as a drug, a receptor ligand, or an antibody.

7. The method according to claim 1, wherein the subject is a whole organism, a sample from an organism, or cells.

8. The method according to claim 1, wherein the imaging the particle comprises in vitro imaging a sample from the subject taken after the particle has been provided to the subject.

9. The method according to claim 8, further comprising utilizing the particle for in vitro cell labeling, in vitro microscopy, in vitro imaging of vascularization or perfusion, or in vitro histology.

10. The method according to claim 1, wherein the imaging the particle comprises in vivo imaging of the particle in the subject.

11. The method according to claim 10, further comprising utilizing the particle for in vivo cell labeling, in vivo microscopy, in vivo imaging of vascularization or perfusion, or in vivo histology.

12. The method according to claim 1, further comprising utilizing the particle for diagnostic imaging, imaging of metastases or vasculature, quantitative imaging, qualitative imaging, therapeutic imaging, imaging of cellular vaccines, imaging of cellular therapeutics, imaging of dendritic cell vaccines, imaging of stem cells, or imaging of beta islet cells.

13. The method according to claim 1, wherein the perfluoro crown ether is perfluoro-15-crown-5-ether.

* * * * *